United States Patent
Blume et al.

(10) Patent No.: US 6,855,714 B2
(45) Date of Patent: Feb. 15, 2005

(54) 1-ALKYL-2-ARYL-BENZIMIDAZOLE DERIVATIVES, THEIR USE FOR THE PRODUCTION OF PHARMACEUTICAL AGENTS AS WELL AS PHARMACEUTICAL PREPARATIONS THAT CONTAIN THESE DERIVATIVES

(75) Inventors: Thorsten Blume, Schildow (DE); Wolfgang Halfbrodt, Berlin (DE); Joachim Kuhnke, Potsdam (DE); Ursula Moenning, Woltersdorf (DE); Herbert Schneider, Berlin (DE); Bernd Elger, Berlin (DE)

(73) Assignee: Schering Aktiengesellschaft, Berlin (DE)

( * ) Notice: Subject to any disclaimer, the term of this patent is extended or adjusted under 35 U.S.C. 154(b) by 0 days.

(21) Appl. No.: 10/189,179

(22) Filed: Jul. 5, 2002

(65) Prior Publication Data

US 2003/0055057 A1 Mar. 20, 2003

Related U.S. Application Data

(60) Provisional application No. 60/347,242, filed on Jan. 14, 2002.

(30) Foreign Application Priority Data

Jul. 6, 2001 (DE) .......................... 101 34 775

(51) Int. Cl.⁷ .................. A61K 31/4184; C07D 235/18
(52) U.S. Cl. .............. 514/253.01; 514/234.5; 514/253.09; 514/254.06; 514/394; 544/139; 544/364; 544/370; 544/359; 546/273.4; 548/310.1; 548/310.7; 548/309.7; 548/304.7; 548/306.1

(58) Field of Search .............. 548/310.1, 310.7, 548/309.7, 304.7, 306.1; 544/139, 364, 370, 359; 546/273.4; 514/394, 234.5, 253.01, 253.09, 254.06

(56) References Cited

U.S. PATENT DOCUMENTS

| 5,552,426 A | 9/1996 | Lunn et al. |
| 2002/0006948 A1 | 1/2002 | Halfbrodt et al. |

FOREIGN PATENT DOCUMENTS

| WO | WO 9507263 | 3/1995 |
| WO | WO 0151473 | 7/2001 |

Primary Examiner—Laura L. Stockton
(74) Attorney, Agent, or Firm—Wendy L. Washtien; Ronald S. Hermenau

(57) ABSTRACT

The invention relates to novel benzimidazole derivatives with general formula I, whereby radicals $R^1$, $R^2$, $R^3$, A, B and Y have the meanings that are indicated in the description and the claims, the use of these compounds for the production of a pharmaceutical agent for treating and for preventing diseases that are associated with microglia activation, as well as pharmaceutical preparations that contain these compounds.

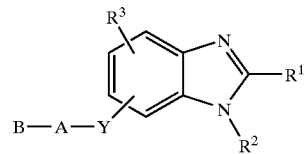

14 Claims, No Drawings

1-ALKYL-2-ARYL-BENZIMIDAZOLE DERIVATIVES, THEIR USE FOR THE PRODUCTION OF PHARMACEUTICAL AGENTS AS WELL AS PHARMACEUTICAL PREPARATIONS THAT CONTAIN THESE DERIVATIVES

This application claims the benefit of the filing date of U.S. Provisional Application Ser. No. 60/347,242 filed Jan. 14, 2002.

The invention relates to new benzimidazole derivatives and the use of benzimidazole derivatives for the production of pharmaceutical agents for treatment of diseases that are associated with a microglia activation and for prevention of these diseases as well as pharmaceutical preparations that contain the new benzimidazole derivatives.

Almost all degenerative diseases of the central nervous system are connected to chronic inflammation. A central step of the inflammation process is the activation of mononuclear phagocyte cells, the microglia. This is carried out in, for example, Alzheimer's disease by senile plaques, in Creutzfeldt-Jakob disease by a prion protein, and in ischemic stroke by dead cells. The microglia can remain for a prolonged period in the activated state, in which they produce and secrete various inflammation factors, for example reactive oxygen/nitrogen intermediate products, proteases, cytokines, complement factors and neurotoxins. The latter in turn produce neuronal dysfunction and degeneration.

To treat inflammations and arteriosclerosis, i.a., benzimidazole derivatives had been proposed as active ingredients:

For example, in EP 0 104 727 A1, benzimidazole derivatives are indicated that are not substituted in 1-position and that have an alkyl group in 2-position. Substituents in the benzene ring of the derivatives are, i.a., pyridyloxy radicals, pyridylalkyl radicals, pyridylalkyloxy radicals and pyridyloxyalkanediyl radicals.

In EP 0 520 200 A2, benzimidazole derivatives are indicated that have aryl radicals that are substituted in 1-position and amino groups that are monosubstituted or disubstituted in 2-position or are unsubstituted. The benzene ring of the benzimidazole skeleton can be substituted with halogen, trifluoromethyl and/or cyano. These compounds are used to treat diseases that are associated with an increased activation of Ca-channels.

In WO 01/21634 A1, benzimidazole derivatives are also described that in 1-position an alkanediylamido group can be substituted with at least one substituted alkoxy, alkylamino, alkylsulfonyl and alkylsulfoxide radical; in 2-position, i.a., a substituted phenyl or heteroaryl radical can be substituted with at least one substituted alkoxy, alkylamino, alkylsulfonyl and alkylsulfoxide radical, and on the anellated benzene ring, i.a., with at least one substituted alkoxy, alkylamino, alkylsulfonyl and alkylsulfoxide radical. It is indicated that these substances can be used for a considerable number of possible indications as active ingredients in pharmaceutical agent preparations.

In U.S. Pat. No. 5,552,426, substituted benzimidazoles are indicated that have in 1-position, i.a., an alkyl radical, and in 2-position, i.a., a phenyl or heteroaryl radical. The anellated benzene ring of the benzimidazoles is preferably substituted with an alkoxy or aminoalkoxy radical. An effectiveness against diseases that are associated with a □-amyloid peptide is ascribed to such compounds.

In WO 97/33873 A1, benzimidazole derivatives are also described that are used to treat cystitis. These compounds can have in 1-position, i.a., phenyl, naphthyl and unsaturated heterocyclic radicals. In 2-position, the derivatives can be substituted with alkoxy radicals, phenylalkoxy radicals, naphthylalkoxy radicals, heterocyclic alkoxy radicals or unsaturated heterocyclic alkoxy radicals. The benzene ring of the skeleton of the derivatives can be substituted with nitro, alkanoyl, amino, alkyl, alkoxy, cycloalkyl, heterocyclic, unsaturated heterocyclic, halo, alkylthio, hydroxyalkylidenyl, hydroxyalkylidenylamino, aminoalkylidenyl, aminoalkoxy, hydroxyalkyl, heterocyclic alkoxy, aminoalkylidenyl or trifluoromethyl radicals.

In WO 97/12613 A1, various agents that have an antiinflammatory action and an arteriosclerosis-prophylactic action are described. For example, benzimidazole derivatives are indicated as active ingredients that are substituted in 1-position, i.a., with an alkyl radical, and in 2-position, i.a., with a phenyl, naphthyl or heteroaryl radical. The substituent in the benzene ring of the active ingredient compounds can be, i.a., an alkoxy radical or an alkylthio radical.

In EP 0 531 833 A1, condensed five-membered heterocycles are indicated, for example substituted benzimidazole derivatives, which are substituted in 1-position, for example, with an alkyl radical and in 2-position, for example, with a substituted phenyl radical. In addition, the described derivatives can have additional substituents on the benzene ring of the benzimidazole skeleton. The anellated benzene ring can then be substituted with, i.a., an alkylenoxy group or alkylenamino group with a terminal carboxyl group. In the very numerous examples, however, only a few benzimidazole derivatives that are substituted in 1-position with an alkyl radical, in 2-position with an aryl or heteroaryl radical and on the anellated benzene ring of the skeleton with the above-mentioned alkylenoxy group or alkylenamino group are expressly mentioned. The described compounds are to have an antithrombic action.

In the publications indicated above, it is only indicated that the described active ingredients are suitable for treating thromboses, arteriosclerosis, cystitis and diseases that are associated with a □-amyloid-peptide as well as with an increased activation of Ca-channels. An effect of the benzimidazole derivatives on microglia is not known from the documents, however.

For a possible treatment of neuroinflammation, to date non-steroidal antiinflammatory agents (COX II inhibitors) [McGeer, P. L.; Roger, Neurology, 42, 447–449 (1992), Rogers, J.; Kirby, L. C.; Hempleman, S. R.; Berry, D. L.; McGeer, P. L.; Kaszniak, A. W.; Zalinski, J.; Cofield, M.; Mansukhani, L.; Wilson, P.; Kogan, F., Neurology 43, 1609–1611 (1993), Andersen, K.; Launer, L. J.; Ott, A.; Hoes, A. W.; Breteler, M. M. B.; Hofman, A., Neurology, 45, 1441–1445 (1995), Breitner, J. C. S.; Gau, B. A.; Welsh, K. A.; Plassman, B. L.; McDonald, W. M.; Helms, M. J.; Anthony, J. C., Neurology, 44, 227–232 (1994), The Canadian Study of Health and Aging, Neurology, 44, 2073–2079 (1994)], cytokine modulators [McGeer, P. L., McGeer, E. G., Brain Res. Rev., 21:195–218 (1995), McGeer, E. G.; McGeer, P. L., CNS Drugs, 7, 214–228 (1997), Barone, F. C. and Feuerstein, G. Z., J. Cerebral Blood Flow and Metabolism, 19, 819–834 (1999)] and complement-cascade-inhibitors (Chen., S.; Frederickson, R. C. A., and Brunden, K. R., Neurobiol. Aging (1996), McGeer, E. G.; McGeer, P. L., Drugs, 55: 739–746 (1998)] have been described.

The problem of this invention is that the known substances inhibit the synthesis or the action of individual inflammation factors without, however, the inflammation process being inhibited in an earlier step. The object therefore consists of finding substances that inhibit an earlier step in the inflammation process and thus prevent the development or the action of many inflammation factors.

The problem is solved by new 1-alkyl-2-aryl-benzimidazole derivatives according to claim 1, also by the use of benzimidazole derivatives for the production of pharmaceutical agents for treating diseases that are associated with microglia as well as for preventing these diseases according to claim 9 as well as pharmaceutical preparations that contain the new benzimidazole derivatives according to claim 10.

The new benzimidazole derivatives have the following general formula I:

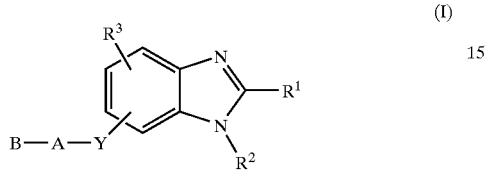

Here:
- $R^1$ is an aryl group or a five- or six-membered heteroaryl group with one or two heteroatoms, selected from the group that comprises N, S and O, a benzothienyl group or an indolyl group, whereby the above-mentioned aryl group or heteroaryl group can be substituted with up to three radicals, independently of one another, selected from the group comprising:
  F, Cl, Br,
  $C(NH)NH_2$, $C(NH)NHR^4$, $C(NH)NR^4R^{4'}$, $C(NR^4)NH_2$, $C(NR^4)NHR^{4'}$, $C(NR^4)NR^4R^{4'}$,
  X—OH, X—$OR^4$, X—$OCOR^4$, X—$OCONHR^4$,
  X—$COR^4$, X—$C(NOH)R^4$,
  X—CN, X—COOH, X—$COOR^4$, X—$CONH_2$, X—$CONR^4R^{4'}$, X—$CONHR^4$,
  X—CONHOH,
  X—$SR^4$, X—$SOR^4$, X—$SO_2R^4$,
  $SO_2NH_2$, $SO_2NHR^4$, $SO_2NR^4R^{4'}$,
  $NO_2$, X—$NH_2$, X—$NHR^4$, X—$NR^4R^{4'}$,
  X—$NHSO_2R^4$, X—$NR^4SO_2R^{4'}$,
  X—$NHCOR^4$, X—$NHCOOR^4$, X—$NHCONHR^4$ and $R^4$,
  whereby X is a bond, $CH_2$, $(CH_2)_2$ or $CH(CH_3)$,
  whereby also radicals $R^4$ and $R^{4'}$ are selected independently of one another according to the meanings that are further indicated below, and
  whereby two radicals at $R^1$, if they are in ortho-position to one another, are linked to one another in such a way that they jointly form a methanediylbisoxy, ethane-1,2-diylbisoxy, propane-1,3-diyl or butane-1,4-diyl group,
- $R^2$ is a radical that is selected from the group that comprises $C_{1-6}$-alkyl, ($C_{0-3}$-alkanediyl-$C_{3-7}$-cycloalkyl) and $C_{3-6}$alkenyl, in which an H atom can be exchanged for a saturated heterocyclic radical that is selected from the group that comprises piperazine, morpholine, piperidine and pyrrolidine in such a way that a bond to a first N atom of the heterocyclic radical is formed,
  whereby the above-mentioned alkyl, cycloalkyl and alkenyl radicals and the heterocyclic radical can be substituted with up to two radicals, selected from the group that comprises $C_{0-2}$-alkanediyl-OH, $C_{0-2}$-alkanediyl-$OR^7$,
  $C_{0-2}$-alkanediyl-$NH_2$, $C_{0-2}$-alkanediyl-$NHR^7$, $C_{0-2}$-alkanediyl-$NR^7R^{7'}$, $C_{0-2}$-alkanediyl-$NHCOR^7$, $C_{0-2}$-alkanediyl-$NR^7COR^{7'}$,
  $C_{0-2}$-alkanediyl-$NHSO_2R^7$, $C_{0-2}$-alkanediyl-$NR^7SO_2R^{7'}$,
  $C_{0-2}$-alkanediyl-$CO_2H$, $C_{0-2}$-alkanediyl-$CO_2R^7$,
  $C_{0-2}$-alkanediyl-$CONH_2$, $C_{0-2}$-alkanediyl-$CONHR^7$, $C_{0-2}$-alkanediyl-$CONR^7R^{7'}$, phenyl and a five- or six-membered heteroaryl radical, whereby the heteroaryl radical contains one or two heteroatoms, selected from the group that comprises N, S and O, whereby also the phenyl radical and the heteroaryl radical can be substituted with up to two radicals, selected from the group that comprises F, Cl, Br, $CH_3$, $C_2H_5$, OH, $OCH_3$, $OC_2H_5$, $NO_2$, $N(CH_3)_2$, $CF_3$, $C_2F_5$ and $SO_2NH_2$ and/or can also carry an anellated methanediylbisoxy group or an ethane-1,2-diylbisoxy group,
  whereby the piperazine radical can be substituted on a second nitrogen atom also with $R^7$, $COR^7$ or $SO_2R^7$,
  whereby $R^7$ and $R^{7'}$, independently of one another, can be selected according to the meanings that are further indicated below,
- $R^3$ is one or two substituents that can be selected independently of one another, selected from the group comprising:
  hydrogen,
  F, Cl, Br,
  OH, $OR^4$, $OCOR^4$, $OCONHR^4$,
  $COR^4$,
  CN, COOH, $COOR^4$, $CONH_2$, $CONHR^4$, $CONR^4R^{4'}$, CONHOH,
  $CONHOR^4$,
  $SR^4$, $SOR^4$, $SO_2R^4$, $SO_2NH_2$, $SO_2NHR^4$, $SO_2NR^4R^{4'}$,
  $NO_2$, $NH_2$, $NHR^4$, $NR^4R^{4'}$,
  $NHSO_2R^4$, $NR^4SO_2R^{4'}$, $NHSO_2R^6$, $NR^4SO_2R^6$,
  $NHCOR^4$, $NHCOOR^4$, $NHCON^4$ and $R^4$,
  whereby radicals $R^4$, $R^{4'}$ and $R^6$, independently of one another, are selected according to the meanings that are further indicated below,
- A is a group that is selected from the group that comprises $C_{1-10}$-alkanediyl, $C_{2-10}$-alkenediyl, $C_{2-10}$-alkinediyl and ($C_{0-3}$-alkanediyl-$C_{3-7}$-cycloalkanediyl-$C_{0-3}$-alkanediyl),
  whereby in a five-membered cycloalkyl ring, a ring member can be ring-N or ring-O and in a six- or seven-membered cycloalkyl ring, one or two ring members can be ring-N and/or ring-O atoms, whereby the ring-N atoms optionally can be substituted with $C_{1-3}$-alkyl or $C_{1-3}$-alkanoyl,
  whereby in the above-mentioned aliphatic chains, a C atom can be exchanged for O, NH, N—$C_{1-3}$-alkyl or N—$C_{1-3}$-alkanoyl and whereby alkyl groups or cycloalkyl groups optionally can be substituted with a radical that is selected from the group that comprises =O, OH, O—$C_{1-3}$-alkyl, $NH_2$, NH—$C_{1-3}$-alkyl, NH—$C_{1-3}$-alkanoyl, N($C_{1-3}$alkyl)$_2$ and N($C_{1-3}$-alkyl)($C_{1-3}$-alkanoyl),
- B is a radical that is selected from the group that comprises COOH, $COOR^5$, $CONH_2$, $CONHNH_2$, $CONHR^5$, $CONR^5R^{5'}$, CONHOH, $CONHOR^5$ and tetrazolyl,
  in each case bonded to a C atom of group A,
  whereby radicals $R^5$ and $R^{5'}$, independently of one another, are selected according to the meanings that are further indicated below,
- Y is a group that is selected from the group that comprises O, NH, $NR^4$, $NCOR^4$, $NSO_2R^4$ and $NSO_2R^6$,
  whereby $R^4$ and $R^6$ have the meanings that are further indicated below, whereby in the above radicals, radicals $R^4$, $R^{4\prime}$, $R^5$, $R^{5\prime}$, $R^6$, $R^7$ and $R^{7\prime}$ have the following meanings; here:

$R^4$ and $R^{4\prime}$, independently of one another, in each case are a radical that is selected from the group that comprises $CF_3$, $C_2F_5$, $C_{1-4}$-alkyl, $C_{2-4}$-alkenyl, $C_{2-3}$-alkinyl and ($C_{0-3}$-alkanediyl-$C_{3-7}$-cycloalkyl), whereby alkyl radicals optionally can be substituted with a radical that is selected from the group that comprises OH, $OCH_3$ and $SCH_3$, and whereby in a five-membered cycloalkyl ring, a ring member can be ring-N or ring-O, and in a six- or seven-membered cycloalkyl ring, one or two ring members can be ring-N and/or ring-O atoms in each case, whereby the ring-N atoms optionally can be substituted with $C_{1-3}$-alkyl or $C_{1-3}$-alkanoyl, $R^5$ and $R^{5\prime}$, independently of one another, in each case are a radical, selected from the group that comprises $C_{1-6}$-alkyl, $C_{2-6}$-alkenyl and $C_{2-6}$-alkinyl, whereby a C atom can be exchanged for O, S, SO, $SO_2$, NH, N—$C_{1-3}$-alkyl or N—$C_{1-3}$-alkanoyl, also ($C_{0-3}$-alkanediyl-$C_{3-7}$-cycloalkyl), whereby in a five-membered cycloalkyl ring, a ring member can be ring-N or ring-O and in a six- or seven-membered cycloalkyl ring, one or two ring members in each case can be ring-N and/or ring-O atoms, whereby the ring-N atoms optionally can be substituted with $C_{1-3}$-alkyl or $C_{1-3}$-alkanoyl, as well as also ($C_{0-3}$-alkanediyl-aryl) and ($C_{0-3}$-alkanediyl-heteroaryl), whereby the heteroaryl group is five- or six-membered and contains one or two heteroatoms, selected from the group that comprises N, S and O, whereby all previously mentioned alkyl and cycloalkyl radicals with up to two radicals, selected from the group that comprises $CF_3$, $C_2F_5$, OH, O—$C_{1-3}$-alkyl, $NH_2$, NH—$C_{1-3}$-alkyl, NH—$C_{1-3}$-alkanoyl, $N(C_{1-3}$-alkyl$)_2$, $N(C_{1-3}$-alkyl)($C_{1-3}$-alkanoyl), COOH, $CONH_2$ and COO—$C_{1-3}$-alkyl, and all previously mentioned aryl and heteroaryl groups can be substituted with up to two radicals, selected from the group that comprises F, Cl, Br, $CH_3$, $C_2H_5$, OH, $OCH_3$, $OC_2H_5$, $NO_2$, $N(CH_3)_2$, $CF_3$, $C_2F_5$ and $SO_2NH_2$ and/or can also carry an anellated methanediylbisoxy- or ethane-1,2-diylbisoxy group, or $R^5$ and $R^{5\prime}$ together with the amide-N atom of B form a five- to seven-membered, saturated or unsaturated heterocyclic ring, which can contain another N or O or S atom, and which can be substituted with $C_{1-4}$-alkyl, ($C_{0-2}$-alkanediyl-$C_{1-4}$-alkoxy), $C_{1-4}$-alkoxycarbonyl, aminocarbonyl or aryl, $R^6$ is a radical that is selected from the group that comprises ($C_{0-3}$-alkanediyl-aryl) and ($C_{0-3}$-alkanediyl-heteroaryl), whereby the heteroaryl group is five- or six-membered and contains one or two heteroatoms, selected from the group that comprises N, S and O, and whereby the aryl and heteroaryl groups can be substituted with up to two radicals, selected from the group that comprises F, Cl, Br, $CH_3$, $C_2H_5$, OH, $OCH_3$, $OC_2H_5$, $NO_2$, $N(CH_3)_2$, $CF_3$, $C_2F_5$, and $SO_2NH_2$ and/or can also carry an anellated methanediylbisoxy group or ethane-1,2-diylbisoxy group, $R^7$ and $R^{7\prime}$, independently of one another, are $R^4$ or $R^6$.

In a preferred embodiment, those derivatives are excluded in which $R^2$ stands for $C_{1-6}$-alkyl, especially methyl, and $R^1$ is substituted with CN or with $C(NH)NH_2$, if Y stands for $NR^4$ and B stands for COOH or $COOR^5$.

This invention also comprises physiologically compatible salts as well as esters of the above-mentioned compounds, especially the acid salts of the nitrogen bases of the benzimidazole derivatives according to the invention, also the salts of carboxylic acids of the derivatives according to the invention with bases, as well as the esters of the carboxylic acids of the derivatives as well as carboxylic acids that are derived from carboxylic acid derivatives, for example from carboxylic acid amides.

The benzimidazole derivatives according to the invention can have a chiral center or several chiral centers, so that the compounds can occur in several isomeric forms. The compounds of Formula I can also be present as tautomers, stereoisomers or geometric isomers. The invention also comprises all possible isomers, such as E- and Z-isomers, S- and R-enantiomers, diastereomers, racemates and mixtures of the same including the tautomeric compounds. All of these isomeric compounds are—unless expressly indicated otherwise in each case—components of this invention. The isomeric mixtures can be separated into enantiomers or E/Z-isomers according to commonly used methods, such as, for example, crystallization, chromatography or salt formation.

The heteroaryl groups that are contained in the benzimidazole compounds according to the invention are built up from five or six skeleton atoms and can contain one or two heteroatoms. Heteroatoms are oxygen (O), nitrogen (N) and sulfur (S). Examples of heteroaryl groups are pyrrolyl, thienyl, furyl, imidazolyl, thiazolyl, isothiazolyl, oxazolyl, isoxazolyl, pyrazolyl, pyridyl, pyrimidinyl, pyrazinyl and pyridazinyl. If the heteroaryl groups are part of $R^1$ or $R^2$, the group is bonded via a C atom to the respective N atom of the benzimidazole skeleton.

As aryl radicals, primarily the phenyl radicals, but also the naphthyl radicals are suitable. The aryl and heteroaryl radicals can be bonded in any way to the benzimidazole skeleton or to another group, for example as 1- or 2-naphthyl, as 2-, 3- or 4-pyridinyl, 2-benzothienyl, 2-thienyl, 3-thienyl, indol-3-yl, 2-furyl, 3-furyl, 2-pyrimidinyl or imidazol-1-yl.

Alkyl groups can be straight-chain or branched. Examples of alkyl groups are methyl, ethyl, n-propyl, iso-propyl, n-butyl, sec-butyl, tert-butyl, n-pentyl, sec-pentyl, tert-pentyl, neo-pentyl, n-hexyl, sec-hexyl, heptyl, octyl, nonyl, and decyl. The higher homologs also comprise respectively both the linear and the branched alkyl groups, thus, for example, 2-ethylhexyl for octyl and 3-propyl-hexyl for nonyl.

Perfluorinated alkyls are preferably $CF_3$ and $C_2F_5$.

Alkenyl groups can be straight-chain or branched. For example, vinyl, 2-propenyl, 1-propenyl, 2-butenyl, 1-butenyl, 1-methyl-1-propenyl, 2-methyl-2-propenyl and 3-methyl-2-propenyl are alkenyl radicals in terms of the invention.

Alkinyl groups can be straight-chain or branched. Examples of this are ethinyl, 1-propinyl, 2-propinyl, 1-butinyl and 2-butinyl.

Cycloalkyl groups are defined in each case preferably as cyclopropyl, cyclobutyl, cyclopentyl, cyclohexyl or cycloheptyl (corresponds to $C_{3-7}$-cycloalkyl).

As a saturated heterocyclic ring or as cycloalkyl with one or more heteroatoms, there are mentioned, for example: piperidine, pyrrolidine, tetrahydrofuran, morpholine, piperazine, hexahydroazepine as well as 2,6-dimethyl-morpholine, N-phenyl-piperazine, methoxymethyl-pyrrolidine, whereby the linkage can be carried out with a C atom that is adjacent to the ring on optionally present ring-N atoms.

Alkanediyl, alkenediyl, alkinediyl and cycloalkanediyl radicals that are mentioned in the description of the invention are the same in meaning as alkylene, alkenylene, alkinylene or cycloalkylene. If in the general formulas of the alkanediyl radicals the number of the C atoms contained is indicated and the value 0 is indicated as a lower limit for the range of this number, this alkanediyl radical is not contained in the respective case.

As alkanes, alkenes and alkines for A, for example, the following are mentioned: straight-chain or branched alkanediyl with one to eight C atoms, for example, methanediyl, ethanediyl, propanediyl, butanediyl, pentanediyl, hexanediyl, also 1-methylethanediyl, 1-ethylethanediyl, 1-methylpropanediyl, 2-methylpropanediyl, 1-methylbutanediyl, 2-methylbutanediyl, 1-ethylbutane-diyl, 2-ethylbutanediyl, 1-methylpentanediyl, 2-methylpentanediyl, 3-methylpentanediyl as well as analogous compounds. Straight-chain or branched alkenediyl and alkinediyl with two to eight C atoms are alkenediyl groups or alkinediyl groups with double and triple bonds in all possible positions as well as with all possible methyl or ethyl substitutions. In these radicals, in each case one or two C atoms can be exchanged for O, NH, N—$C_{1-3}$-alkyl or N—$C_{1-3}$-alkanoyl, whereby the exchanged group is separated from Y by at least two C atoms.

If two radicals are in ortho-position, they can form a common ring with the adjacent aromatic compounds. Compounds in which N, O or S atoms are bonded to olefinic or acetylenic multiple bonds, or in which several N, O, S or halogen atoms are bonded to the same aliphatic C atom, or in which N, O or S atoms are bonded to one another directly, are excluded if these linkages are not defined explicitly, for example in the functional groups that are mentioned in the claim or in heteroaromatic compounds.

The physiologically compatible acid salts of the nitrogen bases of the benzimidazole derivatives according to the invention can be formed with inorganic and organic acids, for example with oxalic acid, lactic acid, citric acid, fumaric acid, acetic acid, maleic acid, tartaric acid, phosphoric acid, hydrochloric acid, hydrobromic acid, sulfuric acid, p-toluenesulfonic acid, and methanesulfonic acid.

For salt formation of acid groups, especially carboxylic acid groups, inorganic or organic bases are also suitable that are known for the formation of physiologically compatible salts, such as, for example, alkali hydroxides, especially sodium and potassium hydroxide, alkaline-earth hydroxides, such as calcium hydroxide, also ammonia, as well as amines, such as ethanolamine, diethanolamine, triethanolamine, N-methylglucamine and tris-(hydroxymethyl)-methylamine.

For ester formation, all lower monovalent, divalent and trivalent alcohols are suitable, especially methanol, ethanol, iso-propanol and tert-butanol as well as ethylene glycol and glycerol.

Especially preferred are benzimidazoles with general formula I, in which the radicals and groups that are indicated below, independently of one another, have the following meanings:

$R^1$ means a phenyl, pyridinyl, thienyl, furanyl, indolyl or benzothienyl group, which can be substituted with up to two of the following radicals, independently of one another, selected from the group comprising:
F, Cl, Br,
$C(NH)NH_2$, $C(NH)NHR^4$, $C(NH)NR^4R^{4'}$, $C(NR^4)NH_2$, $C(NR^4)NHR^{4'}$,
$C(NR^4)NR^4R^{4'}$,
OH, $OR^4$, $OCOR^4$, $OCONHR^4$,
$COR^4$, $C(NOH)R^4$,
CN, COOH, $COOR^4$, $CONH_2$, $CONR^4R^{4'}$, $CONHR^4$, CONHOH,
$SR^4$, $SOR^4$, $SO_2R^4$,
$SO_2NH_2$, $SO_2NHR^4$, $SO_2NR^4R^{4'}$,
$NO_2$, $NH_2$, $NHR^4$, $NR^4R^{4'}$, $NHCONHR^4$ and $R^4$, whereby radicals $R^4$ and $R^{4'}$ are selected independently of one another according to the meanings that are further indicated below and whereby two substituents at $R^1$ are linked to one another in such a way that they jointly form a methanediylbisoxy, ethane-1,2-diylbisoxy, propane-1,3-diyl or butane-1,4-diyl group, if they are in ortho-position to one another, $R^2$ has the same meaning as further indicated above, $R^3$ means a radical that is selected from the group that comprises hydrogen, F, Cl, Br, $CH_3$, $C_2H_5$, $CF_3$, $C_2F_5$, OH, $OR^4$, $NHSO_2R^6$ and $NHCOR^4$, whereby $R^4$ and $R^6$ have the meanings that are further indicated below, A has the same meaning as further indicated above, B means a radical that is selected from the group that comprises COOH, $COOR^5$, $CONH_2$, $CONHR^5$ and $CONR^5R^{5'}$, in each case bonded to a C atom of group A, whereby radicals $R^5$ and $R^{5'}$ are selected independently of one another according to the meanings that are further indicated below, Y means O whereby in the above radicals, radicals $R^4$, $R^{4'}$, $R^5$, $R^{5'}$, $R^6$ and $R^7$ have the following meanings: here:

$R^4$ and $R^{4'}$ have the same meanings as further indicated above, $R^5$ and $R^{5'}$, independently of one another, in each case mean a radical that is selected from the group that comprises $C_{1-6}$-alkyl, $C_{2-6}$-alkenyl, $C_{2-6}$-alkinyl, whereby a C atom can be exchanged for O, S, SO, $SO_2$, NH, N—$C_{1-3}$-alkyl or
N—$C_{1-3}$-alkanoyl, also ($C_{0-3}$-alkanediyl-$C_{3-7}$-cycloalkyl), whereby in a five-membered cycloalkyl ring, a ring member can be ring-N or ring-O, and in a six- or seven-membered cycloalkyl ring, one or two ring members in each case can be ring-N atoms and/or ring-O atoms, whereby ring-N atoms optionally can be substituted with $C_{1-3}$-alkyl or $C_{1-3}$-alkanoyl, as well as also ($C_{0-3}$-alkanediyl-phenyl) and ($C_{0-3}$-alkanediyl-heteroaryl), whereby the heteroaryl group is five- or six-membered and contains one or two heteroatoms, selected from the group that comprises N, S and O, whereby all previously mentioned alkyl and cycloalkyl radicals can be substituted with a radical that is selected from the group that comprises $CF_3$, $C_2F_5$, OH, O—$C_{1-3}$-alkyl, $NH_2$, NH—$C_{1-3}$-alkyl, NH—$C_{1-3}$-alkanoyl, $N(C_{1-3}$-alkyl)$_2$, $N(C_{1-3}$-alkyl)($C_{1-3}$-alkanoyl), COOH, $CONH_2$ and COO—$C_{1-3}$-alkyl, and all previously mentioned phenyl and heteroaryl groups can be substituted with up to two radicals, selected from the group that comprises F, Cl, Br, $CH_3$, $C_2H_5$, OH, $OCH_3$, $OC_2H_5$, $NO_2$, $N(CH_3)_2$, $CF_3$, $C_2F_5$ and $SO_2NH_2$, and/or also can carry an anellated methanediylbisoxy group or ethane-1,2-diylbisoxy group, or $R^5$ and $R^{5'}$ together with the amide-N atom of B form a five- to seven-membered, saturated or unsaturated heterocyclic ring, which can contain another N or O or S atom and which can be substituted with $C_{1-4}$-alkyl, ($C_{0-2}$-alkanediyl-$C_{1-4}$-alkoxy), $C_{1-4}$-alkoxycarbonyl, arninocarbonyl or phenyl, $R^6$ means a phenyl or heteroaryl group, whereby the heteroaryl group is five- or six-membered and contains one or two heteroatoms, selected from the group that comprises N, S and O, and whereby the phenyl and heteroaryl groups can be substituted with up to two radicals, selected from the group that comprises F, Cl, Br, $CH_3$, $C_2H_5$, OH, $OCH_3$, $OC_2H_5$, $NO_2$, $N(CH_3)_2$, $CF_3$, $C_2F_5$ and $SO_2NH_2$, and/or else can carry an anellated methanediylbisoxy group or ethane-1,2-diylbisoxy group, $R^7$ has the same meaning as further indicated above.

Also especially preferred are benzimidazoles with general formula I, in which the radicals and groups that are indicated below have the following meanings:

$R^1$ is a phenyl, pyridinyl, thienyl, furanyl, indolyl or benzothienyl group, which can be substituted with up to two of the following radicals, independently of one another, selected from the group comprising:
F, Cl, Br,
OH, $OR^4$, $OCOR^4$, $OCONHR^4$,
$COR^4$, $C(NOH)R^4$,
COOH, $COOR^4$, $CONH_2$, $CONR^4R^{4'}$, $CONHR^4$, CONHOH,
$SR^4$, $SOR^4$, $SO_2R^4$,
$SO_2NH_2$, $SO_2NHR_4$, $SO_2NR^4R^{4'}$,
$NO_2$,
$R^4$, whereby radicals $R^4$ and $R^{4'}$ are selected independently of one another according to the meanings that are further indicated below, and whereby two substituents can be linked to one another at $R^1$, such that together they form a methanediylbisoxy, ethane-1,2-diylbisoxy, propane-1,3-diyl or butane-1,4-diyl group, if they are in ortho-position to one another, $R^2$ means a radical that is selected from the group that comprises $C_{1-6}$-alkyl, ($C_{0-3}$-alkanediyl-$C_{3-7}$-cycloalkyl) and $C_{3-6}$alkenyl, whereby the above-mentioned alkyl and alkenyl radicals can be substituted, selected from the group that comprises —OH, —$OR^7$, —$NH_2$, —$NHR^7$, —$NR^7R^{7'}$, —$NHCOR^7$, —$NR^7COR^{7'}$, —$NHSO_2R^7$, —$NR^7SO_2R^{7'}$, —$CO_2H$, —$CO_2R^7$, —$CONH_2$, —$CONHR^7$, —$CONR^7R^{7'}$, a saturated heterocyclic radical, selected from the group that comprises piperazine, morpholine, piperidine and pyrrolidine, which is bonded via the N atom, phenyl and a five- or six-membered heteroaryl radical, whereby the heteroaryl radical contains one or two heteroatoms, selected from the group that comprises N, S and O, whereby also the phenyl radical and the heteroaryl radical can be substituted with up to two radicals, selected from the group that comprises F, Cl, Br, $CH_3$, $C_2H_5$, OH, $OCH_3$, $OC_2H_5$, $NO_2$, $N(CH_3)_2$, $CF_3$, $C_2F_5$ and $SO_2NH_2$ and/or can also carry an anellated methanediylbisoxy group or an ethane-1,2-diylbisoxy group, whereby the piperazine radical can be substituted on a second nitrogen atom also with $R^7$, $COR^7$ or $SO_2R^7$, whereby $R^7$ and $R^{7'}$ can be selected independently of one another according to the meanings that are further indicated below, $R^3$ means hydrogen, A means straight-chain or branched alkanediyl with up to 6 C atoms, B means a radical that is selected from the group that comprises COOH, $COOR^5$, $CONH_2$, $CONHR^5$ and $CONR^5R^{5'}$, in each case bonded to a C atom of group A, whereby radicals $R^5$ and $R^{5'}$ are selected independently of one another according to the meanings that are further indicated above, Y means O, whereby in the above radicals, radicals $R^4$, $R^{4'}$, $R^5$, $R^{5'}$, $R^6$ and $R^7$ have the following meanings: here:

$R^1$ and $R^{4'}$, independently of one another, in each case mean a radical that is selected from the group that comprises $CF_3$, $C_2F_5$, $C_{1-4}$-alkyl, $C_{2-4}$-alkenyl, $C_{2-3}$-alkinyl and ($C_{0-3}$-alkanediyl-$C_{3-7}$-cycloalkyl), whereby alkyl radicals optionally can be substituted with a radical that is selected from the group that comprises OH, $OCH_3$ and $SCH_3$, $R^5$ and $R^{5'}$, independently of one another, in each case mean a radical that is selected from the group that comprises $C_{1-6}$alkyl, $C_{2-6}$-alkenyl, $C_{2-6}$-alkinyl, ($C_{0-3}$-alkanediyl-$C_{3-7}$-cycloalkyl), ($C_{0-3}$-alkanediyl-phenyl) and ($C_{0-3}$-alkanediyl-heteroaryl), whereby the heteroaryl group is five- or six-membered and contains one or two heteroatoms, selected from the group that comprises N, S and O, whereby all previously mentioned alkyl and cycloalkyl radicals can be substituted with a radical that is selected from the group that comprises $CF_3$, $C_2F_5$, OH, O—$C_{1-3}$-alkyl, $NH_2$, NH—$C_{1-3}$-alkyl, NH—$C_{1-3}$-alkanoyl, $N(C_{1-3}$-alkyl$)_2$, $N(C_{1-3}$-alkyl)($C_{1-3}$-alkanoyl), COOH, $CONH_2$ and COO—$C_{1-3}$-alkyl, and all previously mentioned phenyl and heteroaryl groups can be substituted with up to two radicals, selected from the group that comprises F, Cl, Br, $CH_3$, $C_2H_5$, OH, $OCH_3$, $OC_2H_5$, $NO_2$, $N(CH_3)_2$, $CF_3$, $C_2F_5$ and $SO_2NH_2$, and/or also can carry an anellated methanediylbisoxy group or ethane-1,2-diylbisoxy group, or $R^5$ and $R^{5'}$ together with the amide-N atom of B form a five- to seven-membered, saturated or unsaturated heterocyclic ring, which can contain another N or O or S atom and which can be substituted with $C_{1-4}$-alkyl, ($C_{0-2}$-alkanediyl-$C_{1-4}$-alkoxy), $C_{1-4}$-alkoxycarbonyl, aminocarbonyl or phenyl, $R^7$ and $R^{7'}$, independently of one another, mean $R^4$ or $R^6$, $R^6$ means a phenyl or heteroaryl group, whereby the heteroaryl group is five- or six-membered and contains one or two heteroatoms, selected from the group that comprises N, S and O, and whereby the phenyl and heteroaryl groups can be substituted with up to two radicals, selected from the group that comprises F, Cl, Br, $CH_3$, $C_2H_5$, OH, $OCH_3$, $OC_2H_5$, $NO_2$, $N(CH_3)_2$, $CF_3$, $C_2F_5$ and $SO_2NH_2$, and/or else can carry an anellated methanediylbisoxy group or ethane-1,2-diylbisoxy group.

The grouping Y—A is set forth in a preferred embodiment by an n-pentanediyloxy group (—$C_5H_{10}$—O—), which is bonded via the O atom to the benzimidazole skeleton. As an alternative, the groupings can also be used with shorter or longer alkanediyl radicals, for example n-butanediyloxy or n-hexanediyloxy. $R^3$ preferably stands for hydrogen.

Terminal group B preferably stands for COOH, COOR, whereby R in particular can be $C_{1-4}$-alkyl, such as methyl, ethyl, iso-propyl or tert-butyl, or an amide group, for example, a $C_{1-6}$-alkylamido group, whereby alkyl in particular can be iso-propyl or iso-butyl, a dialkylamido group, whereby alkyl in particular can be methyl, or a 3-alkoxy-propanediyl-amino group, whereby alkoxy can be a methyloxy, iso-butyloxy or iso-pentyloxy group.

The substituent B—A—Y— is preferably in 5- or 6-position on the benzimidazole skeleton.

Especially preferred benzimidazole derivatives are indicated in Table 1.

The benzimidazole derivatives according to the invention inhibit the activation of microglia. Microglia are defined here as the macrophages of the brain. The invention therefore also relates to the use of these derivatives for the production of pharmaceutical agents for treating diseases that are associated with a microglia activation as well as for the prevention of these diseases. In this case, a corresponding use of such derivatives is also included with general formula I, in which B can also stand for hydrogen, and Y can also stand for a bond.

The compounds of formula I inhibit the activation of the microglia and the production of interleukin 12 (IL 12) and interferon γ (INFγ). The invention therefore also relates to the use of a compound of formula I, as well as optical or geometric isomers thereof or tautomers or physiologically compatible salts thereof for the production of a pharmaceutical agent for treating or preventing a disease that is associated with a microglia activation as well as a disease that is triggered by over-production of IL 12 and IFNγ and for induction of interleukin 10 (IL-10).

Based on their ability to inhibit the activation of microglia and to interrupt the production of IL 12 and TNFα in monocytes/macrophages and the INFγ production in T cells and NK cells and to increase the induction of the IL-10 production, the compounds according to the invention are suitable for treating numerous diseases that are triggered by the intensified production of cytokines, such as, e.g., TNFα, β, IFNγ, IL 2 and IL12, such as inflammatory diseases, autoimmune diseases, allergic and infectious diseases, toxin-induced inflammations, pharmacologically triggered inflammation reactions as well as pathophysiologically relevant inflammation reactions of an origin that is as yet unclear.

Examples of inflammatory and autoimmune diseases are: chronic inflammatory intestinal diseases (inflammatory bowel diseases, Crohn's disease, ulcerative colitis), arthritis, allergic contact dermatitis, psoriasis, pemphigus, asthma, multiple sclerosis, diabetes, type I insulin-dependent diabetes mellitus, rheumatoid arthritis, lupus diseases and other collagenoses, Graves' disease, Hashimoto's disease, "graft-versus-host disease" and transplant rejections.

Examples of allergic, infectious and toxin-triggered and ischemia-triggered diseases are: sarcoidosis, asthma, hypersensitive pneumonitis, sepsis, septic shock, endotoxin shock, toxic shock syndrome, toxic liver failure, ARDS (acute respiratory distress syndrome), eclampsia, cachexia, acute viral infections (e.g., mononucleosis, fulminant hepatitis), and post-reperfusion organ damage.

An example of a pharmacologically triggered inflammation with pathophysiological relevance is the "first dose response" after administration of anti-T-cell antibodies such as OKT3.

An example of systemic inflammation reactions of an origin that is as yet unclear is eclampsia.

Examples of neuroinflammatory diseases that are associated with a microglia activation are AIDS dementia, amyotrophic lateral sclerosis, Creutzfeldt-Jakob disease, Down's syndrome, diffuse Lewy body disease, Huntington's disease, leukoencephalopathy, multiple sclerosis, Parkinson's disease, Pick's disease, Alzheimer's disease, stroke, temporary lobe epilepsy and tumors. The invention therefore also relates to the use of the indicated benzimidazole derivatives for treating these diseases as well as for preventing these diseases.

The action of the benzimidazole derivatives according to the invention in the treatment and prevention of microglia-associated diseases is surprising, since to date benzimidazole derivatives had been described only for the treatment of thromboses and arteriosclerosis [EP 0 531 883 A1, EP 0 104 727 A1, WO 97/12613 A1], cystitis [WO 97/33873 A1] and diseases that are associated with a □-amyloid peptide [U.S. Pat. No. 5,552,426] as well as an increased activation of Ca-channels [EP 0 520 200 A2], but an effect on microglia is not known.

In Example 114, it is described how the inhibition of the microglia activation can be measured. In this case, the microglia can be activated by various stimuli, such as, for example, with A□-peptide [□-Amyloid, Araujo, D. M. and Cotman, C. M., *Brain Res.* 569, 141–145 (1992)], with prion protein, cytokines or by cell fragments [Combs, C. K. et al. (1999), *J. Neurosci.*, 19, 928–939; Wood, P. L. (1998) Neuroinflammation: Mechanisms and Management, Humana Press].

The stimulation with the A□-peptide corresponds to the pathophysiological situation in the case of Alzheimer's disease. In this test, the substances according to the invention showed inhibition of microglia activation in the case of stimulation with the A□-peptide. The inhibition of the microglia activation by the substances according to the invention results in a strong reduction of the cytokine production and secretion, for example of Il1□ and TNF□ (measured by ELISA and mRNA expression analysis) and in a reduced secretion of reactive oxygen/nitrogen intermediate products. Several inflammation factors are thus equally inhibited.

The in-vivo effectiveness of the substances according to the invention is shown in an MCAO model in rats. This model simulates the condition of a stroke. The substances according to the invention reduce the microglia activation, which occurs in the case of acute cerebral lesions in the brains of animals.

The inhibition of cytokine production is represented, for example, by measuring TNFα and interleukin 12 in lipopolysaccharide (LPS)-stimulated THP-1 cells.

The compounds according to the invention inhibit the TNFα and interleukin 12 production in lipopolysaccharide (LPS)-stimulated THP-1 cells. To show the influence of the substances on the T-cell activation, for example, the measurement of the INFγ secretion is used. The compounds according to the invention inhibit the INFγ production of peripheral mononuclear blood cells.

The invention also relates to pharmaceutical agents that contain one or more compounds of general formula I according to the invention as well as one or more vehicles. The pharmaceutical agents or compositions of the invention are produced in a way that is known in the art with the commonly used solid or liquid vehicles or diluents and the commonly used pharmaceutical and technical adjuvants corresponding to the desired type of administration with a suitable dosage. The preferred preparations consist of a form for dispensing that is suitable for oral, enteral or parenteral administration, for example i.p. (intraperitoneal), i.v. (intravenous), i.m. (intramuscular) or percutaneous administration. Such forms for dispensing are, for example, tablets, film tablets, coated tablets, pills, capsules, powders, creams, ointments, lotions, liquids, such as syrups, gels, injectable liquids, for example for i.p., i. V., i.m. or percutaneous injection, etc. In addition, depot forms, such as implantable preparations, as well as suppositories, are also suitable. In this case, depending on their type, the individual preparations release to the body the benzimidazole derivatives according to the invention gradually or all at once in a short time.

For oral administration, capsules, pills, tablets, coated tablets and liquids or other known oral forms for dispensing can be used as pharmaceutical preparations. In this case, the pharmaceutical agents can be formulated in the way that they release the active ingredients either in a short time and pass on to the body or have a depot action, so that a longer-lasting, slow supply of active ingredients to the body is achieved. In addition to at least one benzimidazole derivative, the dosage units can contain one or more pharmaceutically compatible vehicles, for example substances for adjusting the rheology of the pharmaceutical agent, surfactants, solubilizers, microcapsules, microparticles, granulates, diluents, binders, such as starches, sugar, sorbitol and gelatins, also fillers, such as silicic acid and talc, lubricants, dyes, perfumes and other substances.

Corresponding tablets can be obtained, for example, by mixing active ingredient with known adjuvants, for example inert diluents such as dextrose, sugar, sorbitol, mannitol, polyvinylpyrrolidone, explosives such as corn starch or alginic acid, binders such as starch or gelatin, lubricants such as carboxypolymethylene, carboxy methyl cellulose, cellulose acetate phthalate or polyvinyl acetate. The tablets can also consist of several layers.

Coated tablets can be produced accordingly by coating cores that are produced analogously to the tablets with agents that are commonly used in coated tablet coatings, for example polyvinylpyrrolidone or shellac, gum arabic, talc, titanium oxide or sugar. In this case, the shell of the coated tablet can also consist of several layers, whereby the adjuvants that are mentioned above in the case of the tablets can be used.

Capsules that contain active ingredients can be produced, for example, by the active ingredients being mixed with an inert vehicle such as lactose or sorbitol and encapsulated in gelatin capsules.

The benzimidazole derivatives according to the invention can also be formulated in the form of a solution that is intended for oral administration and that in addition to the active benzimidazole derivative contains as components a pharmaceutically compatible oil and/or a pharmaceutically compatible lipophilic surfactant and/or a pharmaceutically compatible hydrophilic surfactant and/or a pharmaceutically compatible water-miscible solvent.

To achieve better bio-availability of the active ingredients according to the invention, the compounds can also be formulated as cyclodextrin clathrates. To this end, the compounds are reacted with □-, □- or □-cyclodextrin or derivatives thereof If creams, ointments, lotions and liquids that can be applied topically are to be used, the latter must be constituted so that the compounds according to the invention are fed to the body in adequate amounts. In these forms for dispensing, adjuvants are contained, for example substances for adjusting the rheology of pharmaceutical agents, surfactants, preservatives, solubilizers, diluents, substances for increasing the permeability of the benzimidazole derivatives according to the invention through the skin, dyes, perfumes and skin protection agents such as conditioners and moisturizers. Together with the compounds according to the invention, other active ingredients can also be contained in the pharmaceutical agents [*Ullmanns Enzyklopädie der technischen Chemie* [*Ullmanns' Encyclopedia of Technical Chemistry*], Volume 4 (1953), pages 1–39; *J. Pharm. Sci.*, 52, 918 ff. (1963); issued by Czetsch-Lindenwald, *Hilfsstoffe für Pharmazie und angrenzende Gebiete* [*Adjuvants for Pharmaceutics and Related Fields*]; *Pharm. Ind.*, 2, 72 ff (1961), Dr. H. P. Fiedler, *Lexikon der Hilfsstoffe für Pharmazie, Kosmetik und angrenzende Gebiete* [*Dictionary of Adjuvants for Pharmaceutics, Cosmetics and Related Fields*], Cantor A G, Aulendorf/Württ., 1971].

The substances according to the invention can also be used in suitable solutions, such as, for example, physiological common salt solution, as infusion or injection solutions. For parenteral administration, the active ingredients can be dissolved or suspended in a physiologically compatible diluent. As diluents, in particular oily solutions, such as, for example, solutions in sesame oil, castor oil and cottonseed oil, are suitable. To increase solubility, solubilizers, such as, for example, benzyl benzoate or benzyl alcohol, can be added.

To formulate an injectable preparation, any liquid vehicle can be used in which the compounds according to the invention are dissolved or emulsified. These liquids frequently also contain substances to regulate viscosity, surfactants, preservatives, solubilizers, diluents and other additives, with which the solution is set to isotonic. Other active ingredients can also be administered together with the benzimidazole derivatives.

It is also possible to incorporate the substances according to the invention in a transdermal system and thus to administer them transdermally. To this end, the benzimidazole derivatives are applied in the form of a depot injection or an implant preparation, for example subcutaneously. Such preparations can be formulated in such a way that a delayed release of active ingredients is made possible. To this end, known techniques can be used, for example depots that dissolve or operate with a membrane. As inert materials, implants can contain, for example, biodegradable polymers or synthetic silicones, for example silicone gum. The benzimidazole derivatives can also be incorporated in, for example, a patch, for percutaneous administration.

The dosage of the substances of general formula I according to the invention is determined by the attending physician and depends on, i.a., the substance that is administered, the method of administration, the disease that,is to be treated and the severity of the disease. The daily dose is no more than 1000 mg, preferably no more than 100 mg, whereby the dose can be given as a single dose to be administered once or divided into two or more daily doses.

The benzimidazole derivatives according to the invention are produced analogously to known processes: Processes for their production are described in, for example, EP 0 531 883 A1. If the production of the starting compounds is not described, the starting compounds are known and commercially available, or the compounds are synthesized analogously to the described processes. Below, the production of several precursors, intermediate products and products is described by way of example.

In the production of the substances according to the invention, for example, the following processes are used:

As possible processes, in addition to others, the following can be mentioned:

1. By reaction of alkylamines (B) with ortho-leaving group-substituted (preferably halogen-substituted) nitrobenzene derivatives, N-aryl-2-nitrobenzenes (C) can be produced under various reaction conditions, such as, for example, by heating the reactants with or without a suitable inert solvent, such as, e.g., alkyl or halo-benzenes. The amine that is used as a reactant can also be used in excess as a solvent. The reactions are performed both without and with bases (for example potassium carbonate or sodium hydride). Other adjuvants, such as, e.g., copper salts, are also used. Examples of the procedures that are indicated here are found in numerous works, such as, for example, in: D. Jerchel, H. Fischer, M. Graft, *Ann. Chem.* 575, 162 (1952), *CAS*, 53 (2138); R.-A. Abramovitch, *Can. J.*

Chem., 38, 2273 (1960).

DIAGRAM 1

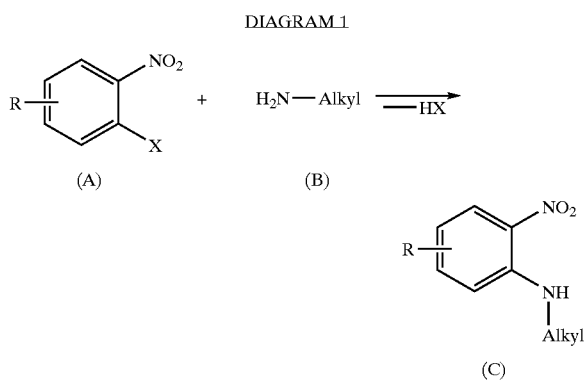

X=Leaving group
R=Substituent(s) or H

The thus obtained N-alkylnitroaniline derivatives can be converted into 1,2-disubstituted benzimidazoles (E) in various ways:

DIAGRAM 2

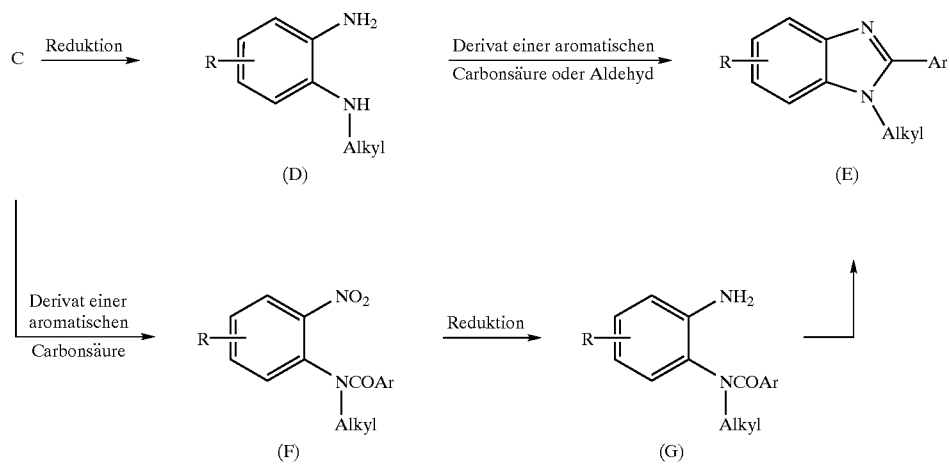

[Key:]
Reduktion=Reduction
Derivat einer aromatischen Carbonsäure oder Aldehyd= Derivative of an aromatic carboxylic acid or aldehyde
Derivat einer aromatischen Carbonsäure=Derivative of an aromatic carboxylic acid The nitro group (C→D or F→G) is preferably reduced by hydrogenation in polar solvents, such as acetic acid, lower alcohols or ethyl acetates, with the addition of catalysts, such as Raney nickel or palladium on carbon, or by chemical reduction, for example with tin in hydrochloric acid, SnCl₂ [F. D. Bellamy, Tet. Lett., (1984)] or Fe/acetic acid [D. C. Owsily, J. J. Bloomfield, Synthesis, 118, 150 (1977)].

Benzimidazoles of type E can be obtained from the diamines of type D by reaction with acid derivatives such as orthoesters, iminoesters, acid anhydrides, aldehydes or else free carboxylic acids with or without acid catalysis and/or dehydrating agents. As an example, the production of 1,2-diphenylbenzimidazole from benzoic acid and N-phenyl-o-phenylenediamine with use of triphenylphosphine oxide and trifluoromethanesulfonic acid anhydride can be indicated here [J. B. Hendrickson, M. S. Hussoin, J. Org. Chem. 52, 4137 (1987)].

The compounds of type C are converted into amides F according to methods that are known in the art with use of suitable acid derivatives, such as, for example, with acid anhydrides or acid chlorides, in suitable solvents, such as aromatic hydrocarbons or halogenated hydrocarbons, with or without the addition of auxiliary bases, such as, for example, triethylamine or pyridine. The closure of the rings of the compounds of type G to type E is carried out according to a process that is known in the art, for example with use of hydrochloric acid, optionally with the addition of a solubilizer, such as a lower alcohol, preferably methanol, or with dehydrating means, such as, for example, polyphosphoric acid, phosphoroxy chloride or the like, optionally with the addition of inert solvents, such as, for example, aromatic or halogenated hydrocarbons, at temperatures of 0° C. to 150° C., preferably 10° C. to 120° C. When using aromatic aldehydes, nitrobenzene is the preferred solvent to be able to perform the oxidation of the primary formed benzimidazoline in situ. For one skilled in the art, it is obvious that substituents R must be compatible with the reagents and the reaction conditions that are used in the course of the synthesis sequence. The substituents optionally can be modified later.

2. A second approach employs direct N-alkylation of pre-fabricated benzimidazoles, for example according to Roth et al., J. Med. Chem., 40, 4199–4207 (1997). For this purpose, a 1H-benzimidazole is deprotonated first with a base such as sodium hydride and then reacted with the electrophilic components such as alkyl halides.

If structural element B—A—Y (Formula I) is established in protected or unprotected form because of incompatibility with the reaction conditions during the respective benzimidazole synthesis or for other reasons of synthesis only after completion of benzimidazole synthesis, various procedures for establishing the B—A—Y structural element (Formula I) are possible depending on substituents $R^3$ that are entrained in the benzene ring of the benzimidazole, whereby, which is obvious to one skilled in the art, a compatibility of the methods used with the aryl substituents and other radicals $R^3$ must be taken into consideration.

Below, some possibilities for establishing the B—A—Y structural element are indicated:

Oxygen can be entrained from the start in free form (e.g., R=OH in Formula (A)) or else in protected form, for example as alkyl ether [cf., for example: B. D. Jerchel, H. Fischer, M. Graft, Ann. Chem., 575, 162 (1952)] as a substituent in a benzimidazole synthesis. By alkyl ether cleavage with, e.g., concentrated hydrobromic acid with the optional aid of solubilizers such as halogenated hydrocarbons or else with boron tribromide in inert solvents, such as, for example, dichloromethane, the hydroxyl group can be released. The hydroxyl function can be reacted according to known methods with optionally one terminal group B (Formula I) or alkyl-, allyl- and benzyl halides that contain a precursor thereof to form the ethers, whereby the reaction is carried out with the alkylating agents preferably in polar solvents, such as, for example, dimethylformamide, dimethyl sulfoxide, ethers, such as, for example, tetrahydrofuran or else lower ketones, such as acetone or methylethyl ketone, with the addition of bases, such as alkali and alkaline-earth hydrides, but preferably sodium hydride, or with the addition of alkali carbonates, such as potassium or cesium carbonate, in a temperature range of 0° C. to 120° C. In addition, a reaction can be carried out in a two-phase system with phase transfer catalysis, whereby the reactants are dissolved in a suitable inert organic solvent, such as, for example, in haloalkanes, but preferably in dichloromethane. The other phase is a solid alkali hydroxide, preferably sodium or potassium hydroxide, or else a concentrated aqueous solution of the hydroxide in question. As phase transfer catalysts, for example, quaternary ammonium salts are used. Reactions under phase transfer catalysis are preferably carried out at room temperature. For example, a compound of Formula A (with R=OH) is dissolved in dimethylformamide and reacted to form a compound of Formula I with the addition of cesium carbonate with 6-bromohexanoic acid methyl ester at temperatures of 0° C. to 50° C. The cleavage of the ester by acidic or alkaline hydrolysis can be carried out according to methods that are known to one skilled in the art, such as, for example, with basic catalysts, such as, for example, with alkali or alkaline-earth carbonates or -hydroxides in an alcohol or the aqueous solution of an alcohol. As alcohols, aliphatic alcohols, such as, for example, methanol, ethanol, butanol, etc., are considered, but preferably methanol. Aqueous solutions of ethers, such as tetrahydrofuran, are also used. As alkali carbonates and alkali hydroxides, lithium, sodium and potassium salts can be mentioned. Preferred are the lithium and sodium salts. As alkaline-earth carbonates and hydroxides, for example, calcium carbonate, calcium hydroxide and barium carbonate are suitable. The reaction is generally carried out at −10° C. to 70° C., but preferably at 25° C. The ester cleavage can also be carried out, however, under acidic conditions, such as, for example, in aqueous hydrochloric acid, optionally with the aid of a solubilizer, such as, for example, a lower alcohol, preferably methanol.

Instead of carboxylic acid groups, the alkylating reagents can also carry phosphonic acid groups or sulfonic acid groups in protected form, from which the corresponding sulfonic acids or phosphonic acids can then be released. In addition, the alkylating reagents in addition to the halogen atom can carry, as another functional group, a tetrazole in protected form, for example tritylated, from which then after alkylation, the tetrazole is released. From a nitrile that is present in the alkylating reagent or else generated later, a tetrazole can also be produced later. To this end, the alkylating product is reacted with an azide, such as, for example, tributyltin azide or sodium azide in a suitable solvent, such as, for example, in aromatic hydrocarbons by heating. Also, a nitrile can be converted by hydrolysis into a carboxylic acid function. The alkylating reagents can also contain functional groups, such as, for example, hydroxyl functions in free or protected form, which after conversion into leaving groups, such as, for example, tosylate, mesylate, bromide or iodide, can be exchanged for, for example, phosphonic acid components, cyanides, amines, alkyl, aryl or heteroaryl components. Also, the alkylating reagents can contain functional groups, such as, for example, halogens or optionally protected amino or mercapto groups.

The establishment of B—A—Y fragments (Formula I) can also be performed, for example, with one of the methods mentioned below.

With the aid of transition metal catalysts such as, for example, tetrakis(triphenylphosphirne)palladium, nickel analogs or other transition metal complexes with or without auxiliary bases, such as, for example, alkali carbonates or alkali bicarbonates in solid form or else as an aqueous solution or else with tertiary amines, halogen substituents (Y=Br, I) or the tin organyls that can be obtained therefrom on benzimidazoles of structure (H):

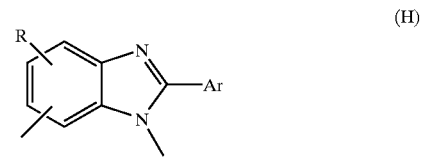

(H)

and hydroxyl groups via their perfluoroalkanesulfonic acid esters (Y=OSO$_2$C$_n$F$_{2n+1}$) can be exchanged in suitable solvents, such as, for example aromatic hydrocarbons, ethers such as tetrahydrofuran or else other solvents, such as, for example, dimethylformamide in the temperature range of 0° C. to 120° C., for example for alkene, alkine, allyl, benzyl or else cyano substituents; cf. for this purpose, for example, F. J. McQuillin et al., "Transition Metal Organometallics for Organic Synthesis," Cambridge University Press 1991, and literature cited there, *Chem. Rev.*, 1989, 43 (89) and literature cited there, *Adv. Chem. ser.*, 1974, 252 (132) or else *Tet. Lett.*, 1986, 1171 (27).

Depending on the substitution desired, substituents R$^3$ are contained in the synthesis components from the start or are established if necessary at suitable sites of the synthesis sequence in question or are generated from suitable precursors that are entrained. Then, nitro groups that are entrained can be reduced to the corresponding amines according to processes already described above and converted into carboxyamino groups.

Sulfonylamino groups are accessible from the amino compounds according to standard processes. Thus, for example, an amine or its hydrochloride is reacted in a suitable inert solvent, such as an aromatic hydrocarbon, for example toluene, or a haloalkane, for example, dichloromethane, with the aid of a base, such as, for example, triethylamine or pyridine, with a sulfonic acid halide at 0° C. to 120° C. Nitriles can be converted, for example, with Grignard reagents or lithium organyls into ketones or hydrolyzed into acids or amides. It is obvious to one skilled in the art that the reaction conditions that are used here must be compatible with the remaining groups that are found in the molecule.

The free acid derivatives of Formula I can be converted according to diverse processes that are known in the literature into amide derivatives or ester derivatives of Formula I. The carboxylic acid ester derivatives of Formula I can be reduced according to diverse processes that are known in the literature to the alcohol derivatives of Formula I, which in turn can be reacted according to diverse processes that are known in the literature to the acylated alcohol derivatives or to urethane or thiourethane derivatives of Formula I.

The free acid derivatives of Formula I can also be converted with neutralization to salts with suitable amounts of the corresponding inorganic bases. For example, when the corresponding acids are dissolved in water, which contains stoichiometric amounts of the base, the solid salt is obtained after the water is evaporated or after a water-miscible solvent, for example alcohol or acetone, is added.

The amine salts can be produced in the usual way. To this end, the corresponding acid is dissolved in a suitable solvent, such as, for example, ethanol, acetone, diethyl ether or benzene, and one to five equivalents of the respective amine is added to this solution. In this case, the salt usually accumulates in solid form or is isolated after the solvent is evaporated in the usual way.

The clathrates with □-, □- or □-cyclodextrin are obtained analogously to the instructions in WO-A-87/05294. □-Cyclodextrin is preferably used. Liposomes are produced according to the process that is described in *Pharmazie in unserer Zeit* [*Pharmaceutics in Our Time*], 11, 98 (1982).

The especially preferred compounds can be found in Table 1:

TABLE 1

Benzimidazole Derivatives

| No. | Benzimidazole Derivative |
|---|---|
| 1 | 1-Benzyl-6-[(5-(Methoxycarbonyl)pentyl)oxy]-2-phenyl-benzimidazole |
| 2 | 1-Benzyl-2-phenyl-6-[(5-(iso-propyloxycarbonyl)pentyl)oxy]-benzimidazole |
| 3 | 1-Benzyl-6-[(5-carboxy-pentyl)oxy]-2-phenyl-benzimidazole |
| 4 | 6-[(5-(Methoxycarbonyl)pentyl)oxy]-1-methyl-2-phenyl-benzimidazole |
| 5 | 6-[(5-(Methoxycarbonyl)pentyl)oxy]-2-phenyl1-n-propyl-benzimidazole |
| 6 | 5-[(5-(Methoxycarbonyl)pentyl)oxy]-2-phenyl1-n-propyl-benzimidazole |
| 7 | 6-[(5-(Methoxycarbonyl)pentyl)oxy]-1-(3-methoxy-n-propyl)-2-phenyl-benzimidazole |
| 8 | 6-[(5-(Methoxycarbonyl)pentyl)oxy]-1-(2-methoxy-ethyl)-2-phenyl-benzimidazole |
| 9 | 6-[(5-Carboxy-pentyl)oxy]-1-(3-methoxy-n-propyl)-2-phenyl-benzimidazole |
| 10 | 6-[(5-Carboxy-pentyl)oxy]-1-(2-methoxy-ethyl)-2-phenyl-benzimidazole |
| 11 | 6-[(5-(Methoxycarbonyl)pentyl)oxy]-2-phenyl-1-iso-propyl-benzimidazole |
| 12 | 1-Cyclohexyl-6-[(5-(methoxycarbonyl)pentyl)oxy]-2-phenyl-benzimidazole |
| 13 | 6-[(5-Carboxy-pentyl)oxy]-1-cyclohexyl-2-phenyl-benzimidazole |
| 14 | 6-[(5-Carboxy-pentyl)oxy]-2-phenyl-1-iso-propyl-benzimidazole |
| 15 | 1-Allyl-5-[(5-(methoxycarbonyl)pentyl)oxy]-2-phenyl-benzimidazole |
| 16 | 1-Allyl-6-[(5-(methoxycarbonyl)pentyl)oxy]-2-phenyl-benzimidazole |
| 17 | 1-Allyl-6-[(5-carboxy-pentyl)oxy]-2-phenyl-benzimidazole |
| 18 | 1-Allyl-5-[(5-carboxy-pentyl)oxy]-2-phenyl-benzimidazole |
| 19 | 5-[(5-(Methoxycarbonyl)pentyl)oxy]-2-phenyl-1-(3-phenyl-prop-2-enyl)-benzimidazole |
| 20 | 6-[(5-(Methoxycarbonyl)pentyl)oxy]-2-phenyl-1-(3-phenyl-prop-2-enyl)-benzimidazole |
| 21 | 1-[3-(4-Fluoro-phenyl)-prop-2-enyl]-5-[(5-(methoxycarbonyl)pentyl)oxy]-2-phenyl-benzimidazole |
| 22 | 1-[(Ethoxycarbonyl)methyl]-6-[(5-(methoxycarbonyl)pentyl)oxy]-2-phenyl-benzimidazole |
| 23 | 1-[(Ethoxycarbonyl)methyl]-5-[(5-(methoxycarbonyl)pentyl)oxy]-2-phenyl-benzimidazole |
| 24 | 1-Cyclohexyl-6-[(5-((3-methyl-butyl)aminocarbonyl)pentyl)oxy]-2-phenyl-benzimidazole |
| 25 | 1-Cyclohexyl-2-phenyl-6-[(5-(iso-propylaminocarbonyl)pentyl)oxy]-benzimidazole |
| 26 | 1-Cyclohexyl-6-[(5-((3-methoxy-propyl)aminocarbonyl)pentyl)oxy]-2-phenyl-benzimidazole |
| 27 | 1-Cyclohexyl-6-[(5-((N,N-dimethylamino)carbonyl)pentyl)oxy]-2-phenyl-benzimidazole |
| 28 | 1-Cyclohexylmethyl-6-[(5-(methoxycarbonyl)pentyl)oxy]-2-phenyl-benzimidazole |
| 29 | 1-Cyclohexylmethyl-5-[(5-(methoxycarbonyl)pentyl)oxy]-2-phenyl-benzimidazole |
| 30 | 1-[(N,N-Dimethylamino)carbonylmethyl]-5-[(5-(methoxycarbonyl)pentyl)oxy]-2-phenyl-benzimidazole |
| 31 | 1-[(N,N-Dimethylamino)carbonylmethyl]-6-[(5-(methoxycarbonyl)pentyl)oxy]-2-phenyl-benzimidazole |
| 32 | 6-[(5-(Methoxycarbonyl)pentyl)oxy]-1-(3-methoxypropyl)-2-(4-methyl-phenyl)-benzimidazole |
| 33 | 6-[(5-(Methoxycarbonyl)pentyl)oxy]-1-(3-methoxypropyl)-2-(4-nitro-phenyl)-benzimidazole |
| 34 | 2-(4-Cyano-phenyl)-6-[(5-(methoxycarbonyl)pentyl)oxy]-1-(3-methoxypropyl)-benzimidazole |
| 35 | 2-(4-Fluoro-phenyl)-6[(5-(methoxycarbonyl)pentyl)oxy]-1-(3-methoxypropyl)-benzimidazole |
| 36 | 6-[(5-(Methoxycarbonyl)pentyl)oxy]-1-(3-methoxy-propyl)-2-(4-trifluoromethyl-phenyl)-benzimidazole |
| 37 | 2-[4-(N,N-Dimethylamino)phenyl]-6-[(5-(methoxycarbonyl)pentyl)oxy]-1-(3-methoxy-propyl)-benzimidazole |
| 38 | 6-[(5-(Methoxycarbonyl)pentyl)oxy]-2-(4-methoxy-phenyl)-1-(3-methoxy-propyl)-benzimidazole |
| 39 | 2-(4-tert-Butyl-phenyl)-6-[(5-(methoxycarbonyl)pentyl)oxy]-1-(3-methoxy-propyl)-benzimidazole |
| 40 | 6-[(5-(Methoxycarbonyl)pentyl)oxy]-1-(3-methoxy-propyl)-2-(4-trifluoromethyloxy-phenyl)-benzimidazole |
| 41 | 6-[(5-(Methoxycarbonyl)pentyl)oxy]-1-(3-methoxy-propyl)-2-(pyrid-3-yl)-benzimidazole |
| 42 | 6-[(5-(Methoxycarbonyl)pentyl)oxy]-1-(3-methoxy-propyl)-2-(pyrid-4-yl)-benzimidazole |

TABLE 1-continued

Benzimidazole Derivatives

| No. | Benzimidazole Derivative |
|---|---|
| 43 | 6-[(5-(Methoxycarbonyl)pentyl)oxy]-1-(3-methoxy-propyl)-2-(thien-2-yl)-benzimidazole |
| 44 | 6-[(5-(Methoxycarbonyl)pentyl)oxy]-1-(3-methoxy-propyl)-2-(thien-3-yl)-benzimidazole |
| 45 | 2-(Indol-3-yl)-6-[(5-(methoxycarbonyl)pentyl)oxy]-1-(3-methoxy-propyl)-benzimidazole |
| 46 | 2-(Fur-2-yl)-6-[(5-(methoxycarbonyl)pentyl)oxy]-1-(3-methoxy-propyl)-benzimidazole |
| 47 | 2-(Fur-3-yl)-6-[(5-(methoxycarbonyl)pentyl)oxy]-1-(3-methoxy-propyl)-benzimidazole |
| 48 | 1-((N,N-Diethylamino)carbonylmethyl)-5-[(5-(methoxycarbonyl)pentyl)oxy]-2-phenyl-benzimidazole |
| 49 | 1-((N,N-Diethylamino)carbonylmethyl)-6-[(5-(methoxycarbonyl)pentyl)oxy]-2-phenyl-benzimidazole |
| 50 | 6-[(5-(Methoxycarbonyl)pentyl)oxy]-1-(3-methoxy-propyl)-2-[2-(methyl)benzothien-3-yl]-benzimidazole |
| 51 | 2-(4-Hydroxy-phenyl)-6-[(5-(methoxycarbonyl)pentyl)oxy]-1-(3-methoxy-propyl)-benzimidazole |
| 52 | 6-[(5-Carboxy-pentyl)oxy]-1-(3-methoxy-propyl)-2-(4-nitro-phenyl)-benzimidazole |
| 53 | 6-[(5-Carboxy-pentyl)oxy]-2-(4-cyano-phenyl)-1-(3-methoxy-propyl)-benzimidazole |
| 54 | 6-[(5-Carboxy-pentyl)oxy]-2-(4-fluoro-phenyl)-1-(3-methoxy-propyl)-benzimidazole |
| 55 | 6-[(5-Carboxy-pentyl)oxy]-1-(3-methoxy-propyl)-2-(4-trifluoromethyl-phenyl)-benzimidazole |
| 56 | 6-[(5-Carboxy-pentyl)oxy]-2-(4-(N,N-dimethylamino)phenyl]-1-(3-methoxy-propyl)-benzimidazole |
| 57 | 6-[(5-Carboxy-pentyl)oxy]-2-(4-methoxy-phenyl)-1-(3-methoxy-propyl)-benzimidazole |
| 58 | 2-(4-tert-Butyl-phenyl)-6-[(5-carboxy-pentyl)oxy]-1-(3-methoxy-propyl)-benzimidazole |
| 59 | 6-[(5-Carboxy-pentyl)oxy]-1-(3-methoxy-propyl)-2-(4-trifluoromethyloxyphenyl)-benzimidazole |
| 60 | 6-[(5-Carboxy-pentyl)oxy]-1-(3-methoxy-propyl)-2-(pyrid-3-yl)-benzimidazole |
| 61 | 6-[(5-Carboxy-pentyl)oxy]-1-(3-methoxy-propyl)-2-(pyrid-4-yl)-benzimidazole |
| 62 | 6-[(5-Carboxy-pentyl)oxy]-1-(3-methoxy-propyl)-2-(thien-2-yl)-benzimidazole |
| 63 | 6-[(5-Carboxy-pentyl)oxy]-1-(3-methoxy-propyl)-2-(thien-3-yl)-benzimidazole |
| 64 | 2-(Indol-3-yl)-6-[(5-carboxy-pentyl)oxy]-1-(3-methoxy-propyl)-benzimidazole |
| 65 | 6-[(5-Carboxy-pentyl)oxy]-2-(fur-3-yl)-1-(3-methoxy-propyl)-benzimidazole |
| 66 | 6-[(5-Carboxy-pentyl)oxy]-2-(fur-2-yl)-1-(3-methoxy-propyl)-benzimidazole |
| 67 | 1-Carboxymethyl-6-[(5-carboxy-pentyl)oxy]-2-phenyl-benzimidazole |
| 68 | 1-Carboxymethyl-5-[(5-carboxy-pentyl)oxy]-2-phenyl-benzimidazole |
| 69 | 6-[(5-Carboxy-pentyl)oxy]-2-phenyl-1-(3-phenyl-prop-2-enyl)-benzimidazole |
| 70 | 5-[(5-Carboxy-pentyl)oxy]-2-phenyl-1-(3-phenyl-prop-2-enyl)-benzimidazole |
| 71 | 1-Cyclohexyl-6-[(5-((3,3-dimethyl-ethyl)aminocarbonyl)pentyl)oxy]-2-phenyl-benzimidazole |
| 72 | 5-[(5-Carboxy-pentyl)oxy]-1-[((N,N-dimethylamino)-carbonyl)methyl]-2-phenyl-benzimidazole |
| 73 | 6-[(5-Carboxy-pentyl)oxy]-1-[((N,N-dimethylamino)-carbonyl)methyl]-2-phenyl-benzimidazole |
| 74 | 6-[(5-Carboxy-pentyl)oxy]-1-(3-methoxy-propyl)-2-(4-methyl-phenyl)-benzimidazole |
| 75 | 5-[(5-Carboxy-pentyl)oxy]-1-[((N,N-diethylamino)-carbonyl)methyl]-2-phenyl-benzimidazole |
| 76 | 6-[(5-Carboxy-pentyl)oxy]-1-(3-methoxy-propyl)-2-[3-methyl-benzothien-2-yl]-benzimidazole |
| 77 | 6-[(5-Carboxy-pentyl)oxy]-2-(4-hydroxy-phenyl)-1-(3-methoxy-propyl)-benzimidazole |
| 78 | 1-(3-Methoxy-propyl)-6-[(5-((3-methoxy-propyl)aminocarbonyl)pentyl)oxy]-2-(4-nitro-phenyl)-benzimidazole |
| 79 | 2-(4-Cyano-phenyl)-1-(3-methoxy-propyl)-6-[(5-((3-methoxy-propyl)aminocarbonyl)pentyl)oxy]-benzimidazole |
| 80 | 2-(4-Fluoro-phenyl)-1-(3-methoxy-propyl)-6-[(5-((3-methoxy-propyl)aminocarbonyl)pentyl)oxy]-benzimidazole |
| 81 | 1-(3-Methoxy-propyl)-6-[(5-((3-methoxy-propyl)aminocarbonyl)pentyl)oxy]-2-(4-trifluoromethyl-phenyl)-benzimidazole |
| 82 | 2-(4-(N,N-Dimethylamino)phenyl)-1-(3-methoxy-propyl)-6-[(5-((3-methoxy-propyl)amino-carbonyl)pentyl)oxy]-benzimidazole |
| 83 | 2-(4-Methoxy-phenyl)-1-(3-methoxy-propyl)-6-[(5-((3-methoxy-propyl)aminocarbonyl)pentyl)-oxy]-benzimidazole |
| 84 | 2-(4-tert-Butyl-phenyl)-1-(3-methoxy-propyl)-6-[(5-((3-methoxy-propyl)aminocarbonyl)pentyl)oxy-benzimidazole |
| 85 | 1-(3-Methoxy-propyl)-6-[(5-((3-methoxy-propyl)aminocarbonyl)pentyl)oxy]-2-(4-trifluoromethyloxy-phenyl)-benzimidazole |
| 86 | 1-(3-Methoxy-propyl)-6-[(5-((3-methoxy-propyl)aminocarbonyl)pentyl)oxy]-2-(4-methyl-phenyl)-benzimidazole |
| 87 | 6-[(5-(Methoxycarbonyl)pentyl)oxy]-2-(4-methoxy-phenyl)-1-[3-morpholin-4-yl-propyl]-benzimidazole |
| 88 | 1-(3-Hydroxy-propyl)-6-[(5-(methoxycarbonyl)pentyl)oxy]-2-(4-methoxy-phenyl)-benzimidazole |
| 89 | 1-(3-Carboxy-ethyl)-6-[(5-(methoxycarbonyl)pentyl)oxy]-2-(4-methoxy-phenyl)-benzimidazole |

TABLE 1-continued

Benzimidazole Derivatives

| No. | Benzimidazole Derivative |
|---|---|
| 90 | 1-(3-Methoxycarbonyl-ethyl)-6-[(5-(methoxycarbonyl)pentyl)oxy]-2-(4-methoxy-phenyl)-benzimidazole |
| 91 | 1-(3-(N,N-Diethylamino)propyl)-6-[(5-(methoxycarbonyl)pentyl)oxy]-2-(4-methoxy-phenyl)-benzimidazole |
| 92 | 6-[(5-(Methoxycarbonyl)pentyl)oxy]-2-(4-methoxy-phenyl)-1-[3-pyrrolidin-1-yl-propyl]-benzimidazole |
| 93 | 6-[(5-(Methoxycarbonyl)pentyl)oxy]-2-(4-methoxy-phenyl)-1-[3-piperidin-1-yl-propyl]-benzimidazole |
| 94 | 6-[(5-(Methoxycarbonyl)pentyl)oxy]-1-[3-(N,N-bis(2-methoxyethyl)amino)-propyl]-2-(4-methoxy-phenyl)-benzimidazole |
| 95 | 6-[(5-(Methoxycarbonyl)pentyl)oxy]-2-(4-methoxy-phenyl)-1-[3-(4-pyrid-2-yl-piperazin-1-yl)-propyl]-benzimidazole |
| 96 | 6-[(5-(Methoxycarbonyl)pentyl)oxy]-2-(4-methoxy-phenyl)-1-[3-(4-phenyl-piperazin-1-yl)-propyl]-benzimidazole |
| 97 | 6-[(5-(Methoxycarbonyl)pentyl)oxy]-2-(4-methoxy-phenyl)-1-[3-(4-methyl-piperazin-1-yl)-propyl]-benzimidazole |
| 98 | 6-[(5-(Methoxycarbonyl)pentyl)oxy]-2-(4-methoxy-phenyl)-1-[3-(4-pyrimid-2-yl-piperazin-1-yl)-propyl]-benzimidazole |
| 99 | 6-[(5-(Methoxycarbonyl)pentyl)oxy]-2-(4-methoxy-phenyl)-1-[3-(3-imidazol-1-yl-propylamino)propyl]-benzimidazole |
| 100 | 6-[(5-(Methoxycarbonyl)pentyl)oxy]-2-(4-methoxy-phenyl)-1-[3-(4-(fur-2-ylcarbonyl)-piperazin-1-yl)-propyl]-benzimidazole |
| 101 | 6-[(5-(Methoxycarbonyl)pentyl)oxy]-2-(4-methoxy-phenyl)-1-[3-(2-hydroxyl-ethyl)amino-propyl]-benzimidazole |
| 102 | 1-[3-(4-(2-Hydroxyethyl)piperazin-1-yl)propyl]-6-[(5-(methoxycarbonyl)pentyl)oxy]-2-(4-methoxy-phenyl)-benzimidazole |
| 103 | 6-[(5-(Methoxycarbonyl)pentyl)oxy]-2-(4-methoxy-phenyl)-1-[3-imidazol-1-yl-propyl]-benzimidazole |
| 104 | 6-[(5-(Methoxycarbonyl)pentyl)oxy]-2-(4-methoxy-phenyl)-1-[3-(N-methyl-N-(methylcarbonyl)amino)propyl]-benzimidazole |
| 105 | 6-[(5-(Methoxycarbonyl)pentyl)oxy]-2-(4-methoxy-phenyl)-1-(3-[N-methyl-N-(trifluoromethylcarbonyl)amino)propyl]-benzimidazole |
| 106 | 6-[(5-(Methoxycarbonyl)pentyl)oxy]-2-(4-methoxy-phenyl)-1-(3-[N-methyl-N-(methylsulfonyl)amino)propyl]-benzimidazole |
| 107 | 6-[(5-(Methoxycarbonyl)pentyl)oxy]-2-(4-methoxy-phenyl)-1-[3-(N-methyl-N-((2-methylthio-ethyl)carbonyl)amino)-propyl]-benzimidazole |
| 108 | 6-[(5-(Methoxycarbonyl)pentyl)oxy]-2-(4-methoxy-phenyl)-1-(3-[N-methyl-N-(trimethylmethylcarbonyl)amino)propyl]-benzimidazole |
| 109 | 6-[(5-(Methoxycarbonyl)pentyl)oxy]-2-(4-methoxy-phenyl)-1-[3-(N-methyl-N-(ethylcarbonyl)amino)propyl]-benzimidazole |
| 110 | 6-[(5-(Methoxycarbonyl)pentyl)oxy]-2-(4-methoxy-phenyl)-1-[3-(N-methyl-N-(fur-2-yl-carbonyl)amino)propyl]-benzimidazole |
| 111 | 6-[(5-(Methoxycarbonyl)pentyl)oxy]-2-(4-methoxy-phenyl)-1-[3-(N-methyl-N-(dimethylmethylcarbonyl)amino)propyl]-benzimidazole |
| 112 | 6-[(5-(Methoxycarbonyl)pentyl)oxy]-2-(4-methoxy-phenyl)-1-[3-(N-methyl-N-(methoxymethylcarbonyl)amino)propyl]-benzimidazole |
| 113 | 6-[(5-(Methoxycarbonyl)pentyl)oxy]-2-(4-methoxy-phenyl)-1-[3-(N-methyl-N-(pyrid-3-yl-carbonyl)amino)propyl]-benzimidazole |

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosure(s) of all applications, patents and publications, cited above or below, and of U.S. Provisional Application Ser. No. 60/3437,242, filed Jan. 14, 2002, are hereby incorporated by reference.

Below, the production of several precursors, intermediate products and products is described by way of example. If the production of the starting compounds is not described, the starting compounds are known and commercially available, or the compounds are synthesized analogously to the described processes.

General Operating Instructions 1:
Nucleophilic Aromatic Substitution on Fluorine/Nitro-Aromatic Compounds:

A mixture that consists of 20 mmol of a 3-fluoro-4-nitro-phenol derivative is heated for four hours to 70° C. with 80 mmol of a primary amine without a solvent. After cooling, it is poured onto an ethyl acetate/water mixture. It is washed with saturated ammonium chloride solution, extracted with ethyl acetate, dried on sodium sulfate, filtered, and the solvent is removed in a vacuum in a rotary evaporator. The crude product that is obtained is used in the next reaction without further purification.

General Operating Instructions 2:
Alkylation of Hydroxybenzimidazole Derivatives and Phenol Derivatives with Alkyl Halides A solution of 1.85 mmol of the phenol derivative in 12 ml of N,N-dimethylformamide is mixed with 1.85 mmol of cesium carbonate and 2.24 mmol of alkyl bromide or alkyl iodide. When alkyl bromides are used, optionally 1.85 mmol of sodium iodide is added. It is stirred for 12 to 96 hours, then poured onto water, taken up with ethyl acetate, the organic phase is washed four times with water, the latter is dried on sodium sulfate and concentrated by evaporation in a vacuum. As an alternative to this aqueous working-up, the reaction mixture can be mixed with dichloromethane, separated from the precipitating salts by filtration, and the filtrate can be concentrated by evaporation in a vacuum. Regardless of the working-up method, the residue is purified by crystallization or column chromatography on silica gel.

General Operating Instructions 3:
Reduction of Nitro Groups, Hydrogenation of Olefinic Double Bonds and Hydrogenolytic Cleavage of Benzyl Ethers The compound that is to be reduced is dissolved in ethyl acetate, tetrahydrofuran, methanol or ethanol or mixtures of the solvent, and hydrogenated to 2 to 5% (relative to the nitro compound) of palladium on carbon (10%) at normal pressure. After hydrogen absorption has ended, it is suctioned off, the residue is washed with ethyl acetate or methanol or ethanol, and the filtrate is concentrated by evaporation in a vacuum. The crude product is generally reacted without further purification.

General Operating Instructions 4:
Cyclization to Benzimidazoles with Aldehydes 1 mmol of a 1,2-diaminobenzene derivative is dissolved in 3 ml of nitrobenzene. 1 mmol of an aryl or heteroaryl-aldehyde is added to this. It is heated for 2 to 6 hours to 150° C. and allowed to cool. The residue is purified directly by column chromatography on silica gel without further working-up.

General Operating Instructions 5:
Saponification of Carboxylic Acid Alkyl Esters 0.77 mmol of the carboxylic acid alkyl ester is dissolved in 5 ml of methanol and 5 ml of tetrahydrofuran and mixed with 5 ml of a 0.5N aqueous lithium or sodium hydroxide solution. After 2 to 12 hours of stirring, it is concentrated by evaporation in a vacuum to a very large extent, neutralized by the addition of aqueous hydrochloric acid and extracted with ethyl acetate. It is dried on sodium sulfate and concentrated by evaporation in a vacuum. The residue is purified, if necessary, by column chromatography on silica gel.

General Operating Instructions 6:
Base-Catalyzed N-Substitution of Benzimidazoles 5 mmol of an N-unsubstituted benzimnidazole derivative is dissolved in 20 ml of dimethylacetamide. 25 mmol of sodium hydride and 20 mmol of an electron-free alkyl-halide are added, and it is stirred for 4 to 72 hours in a moisture-free environment at room temperature, then silica gel is added, it is evaporated to the dry state in a vacuum, and the remaining powder is purified by chromatography on silica gel. Regioisomeric N-alkylation products are separated, if necessary, by means of HPLC.

General Operating Instructions 7:
Amide Formation from Esters Catalyzed by Lewis Acid 0.11 ml of a 2N trimethylaluminum solution [2N in toluene] is added in drops to a solution of 0.22 mmol of a primary or secondary amine in 2 ml of toluene at room temperature. It is allowed to stir for 15 more minutes and then a solution of 0.2 mmol of the corresponding ester in 2 ml of toluene is added in drops. It is heated for 3 to 8 hours (depending on the conversion) to 95° C. The crude products are taken up directly on diatomaceous earth without further working-up and separated by chromatography.

General Operating Instructions 8:
Reductive Amination of Aldehydes 0.35 mmol of sodium triacetoxy borohydride is added at room temperature to a solution of 0.23 mmol of an aldehyde and 0.26 mmol of a primary or secondary amine in 5 ml of tetrahydrofuran. It is allowed to stir for 8 more hours at room temperature. The crude products are taken up directly on diatomaceous earth without further working-up and separated by chromatography.

General Operating Instructions 9:
Acylation of Amines 0.15 mmol of an acid chloride or anhydride is added at 0° C. to a solution of 0.14 mmol of a primary or secondary amine and 0.42 mmol of triethylamine in 3 ml of dichloromethane. It is allowed to stir for 30 more minutes at room temperature. The crude products are taken up directly on diatomaceous earth without further working-up and separated by chromatography.

General Operating Instructions 10:
Cyclization to Benzimidazoles with Orthoesters 10 mmol of a 1,2-diaminobenzene derivative is dissolved in 25 ml of ethanol. 47 ml of an 0.8 M ethereal HCl solution is added in drops to this, stirred for 30 minutes and then evaporated to the dry state in a vacuum. The residue is taken up in 230 ml of methanol and mixed with 6 ml of trimethylorthobenzoate or the corresponding amount of another orthoester. It is refluxed for 2 to 8 hours, poured after cooling on saturated sodium bicarbonate solution, extracted three times with ethyl acetate, the combined extracts are dried on sodium sulfate and concentrated by evaporation in a vacuum. The residue is purified by crystallization or column chromatography on silica gel.

DETAILED EMBODIMENTS FOR SELECTED COMPOUNDS

Sample Compound 1

1-Benzyl-6-[(5-(methoxycarbonyl)pentyl)oxy-2-phenyl-benzimidazole a) 50 g of 3,4-dinitrochlorobenzene is dissolved in 250 ml of ethanol. 82 ml of benzylamine is stirred into the solution, allowed to stand for 24 hours, the crystalline product is suctioned off, washed three times with 2N aqueous hydrochloric acid and dried in a vacuum. N-Benzyl-5-chloro-2-nitroaniline is obtained as an orange-colored solid.

b) 11 g of sodium is dissolved in 850 ml of methanol, 49 g of N-benzyl-5-chloro-2-nitroaniline is added and refluxed for 72 hours. After cooling, it is suctioned off, and the crystallizate is washed with cold methanol. N-Benzyl-5-methoxy-2-nitroaniline is obtained as an orange-colored solid.

c) N-Benzyl-5-methoxy-2-nitroaniline is hydrogenated according to general operating instructions 3. In this case, $N^2$-benzyl-4-methoxybenzene-1,2-diamine is obtained as a black oil.

d) $N^2$-Benzyl-4-methoxybenzene-1,2-diamine is reacted with trimethylorthobenzoate according to general operating instructions 10 to form benzimidazole. 1-Benzyl-6-methoxy-2-phenylbenzimidazole is obtained as a solid.

e) 170 mg of 1-benzyl-6-methoxy-2-phenylbenzimidazole is heated in 5.5 ml of 43% by weight of hydrobromic acid for 1 hour to 140° C. After cooling, it is suctioned off, taken up with ethyl acetate and saturated sodium bicarbonate solution, the organic phase is dried on sodium sulfate and concentrated by evaporation in a vacuum. 1-Benzyl-6-hydroxy-2-phenylbenzimidazole is obtained as a solid.

f) 1-Benzyl-6-hydroxy-2-phenylbenzimidazole is alkylated with 6-bromo-hexanoic acid methyl ester according to general operating instructions 2. 1-Benzyl-6-[(5-(methoxycarbonyl)pentyl)oxy]-2-pentyl-benzimidazole is obtained as a resin.

$^1$H-NMR (CDCl$_3$): δ=1.43–1.55 ppm m (2H); 1.63–1.85 m (4H); 2.36 t (J=7.5 Hz, 2H); 3.67 s (3H); 3.92 t (J=7.5 Hz, 2H); 5.41 s (2H); 6.63 d (J=2 Hz, 1H); 6.95 (dd, J=8.2 Hz, 1H); 7.12 dd (J=8.2 Hz, 2H); 7.30–7.48 m (6H); 7.62–7.69 m (2H); 7.75 d (J=8 Hz, 1H).

Sample Compound 2

1-Benzyl-2-phenyl-6-[(5-(isopropyloxycarbonyl)pentyl]oxy]-benzimidazole

1-Benzyl-6-hydroxy-2-phenylbenzimidazole is alkylated according to general operating instructions 2 with 6-bromo-hexanoic acid isopropyl ester. 1-Benzyl-2-phenyl-6-[(5-(isopropyl-oxycarbonyl)pentyl]oxy]-benzimidazole is obtained as a resin.

$^1$H-NMR (CDCl$_3$): δ=1.22 ppm d (J=8 Hz, 6H); 1.42–1.55 ppm m (2H); 1.62–1.84 m (4H); 2.30 t (J=7.5 Hz, 2H); 3.93 t (J=7.5 Hz, 2H); 5.01 sp (J=8 Hz, 1H); 5.43 s (2H); 6.66 d (J=2 Hz, 1H); 6.94 dd (J=8.2 Hz, 1H); 7.10 dd (J=8.2 Hz, 2H); 7.32–7.48 m (6H); 7.62–7.70 m (2H); 7.75 d (J=8 Hz, 1H).

Sample Compound 3

1-Benzyl-6-[(5-carboxy-pentyl)oxy]-2-phenyl-benzimidazole

1-Benzyl-6-[(5-(methoxycarbonyl)pentyl)oxy]-2-phenyl-benzimidazole is saponified according to general operating instructions 5. 1-Benzyl-6-[(5-carboxy-pentyl)oxy]-2-phenyl-benzimidazole is obtained as a solid.

Flash point 94–98° C.

Sample Compound 7

6-[(5-(Methoxycarbonyl)pentyl)oxy]-1-(3-methoxy-n-propyl)-2-phenyl-benzimidazole a) 3-Fluoro-4-nitrophenol is reacted with 3-methoxypropylamine according to general operating instructions 1. 3-(3-Methoxypropylamino)-4-nitrophenol is obtained as a reddish oil, which is further processed in crude form.
b) 3-(3-Methoxypropylamino)-4-nitrophenol is alkylated according to general operating instructions 2 with 6-bromo-hexanoic acid methyl ester. 6-[3-(3-Methoxypropylamino)-4-nitrophenoxy]hexanoic acid methyl ester is obtained as a yellow oil.
c) 6-[3-(3-Methoxypropylamino)-4-nitro-phenoxy]hexanoic acid methyl ester is hydrogenated according to general operating instructions 3. In this case, 6-[3-(3-methoxypropylanimo)-4-amino-phenoxy]hexanoic acid methyl ester is obtained as a black oil.
d) 6-[3-(3-Methoxypropylamino)-4-amino-phenoxy]hexanoic acid methyl ester is reacted with trimethylorthobenzoate according to general operating instructions 10 to form benzimidazole. 6-[(5-(Methoxycarbonyl)pentyl)oxy]-1-(3-methoxy-n-propyl)-2-phenyl-benzimidazole is obtained as a solid.
Flash point 68–70° C.

Sample Compound 9

6-[(5-Carboxy-pentyl)oxy]-1-(3-methoxy-n-propyl)-2-phenyl-benzimidazole

6-[(5-(Methoxycarbonyl)pentyl)oxy]-1-(3-methoxy-n-propyl)-2-phenyl-benzimidazole is saponified according to general operating instructions 5. 6-[(5-Carboxy-pentyl)oxy]-1-(3-methoxy-n-propyl)-2-phenyl-benzimnidazole is obtained as a solid.

Flash point 128–130° C.

Sample Compound 12

1-Cyclohexyl-6-[(5-(methoxycarbonyl)pentyl)oxy]-2-phenyl-benzimidazole a) 3-Fluoro-4-nitrophenol is reacted with cyclohexylamine according to general operating instructions 1. 3-(Cyclohexylamino)-4-nitrophenol is obtained as a solid.
b) 3-(Cyclohexylamino)-4-nitrophenol is alkylated with 6-bromo-hexanoic acid methyl ester according to general operating instructions 2. 6-[3-(Cyclohexylamino)-4-nitrophenoxy]hexanoic acid methyl ester is obtained as a yellow oil.
c) 6-[3-(Cyclohexylamino)-4-nitrophenoxy]hexanoic acid methyl ester is hydrogenated according to general operating instructions 3. In this case, 6-[3-(cyclohexylamino)-4-amino-phenoxy]hexanoic acid methyl ester is obtained as a black oil.
d) 6-[3-(Cyclohexylamino)-4-amino-phenoxy]hexanoic acid methyl ester is reacted with trimethylorthobenzoate according to general operating instructions 10 to form benzimidazole. 1-Cyclohexyl-6-[(5-(methoxycarbonyl)pentyl)oxy]-2-phenyl-benzimidazole is obtained as a solid.

Flash point 88° C.

Sample Compound 13

6-[(5-(Carboxy-pentyl)oxy]-1-cyclohexyl-2-phenyl-benzimidazole

1-Cyclohexyl-6-[(5-(methoxycarbonyl)pentyl)oxy]-2-phenyl-benzimidazole is saponified according to general operating instructions 5. 6-[(5-(Carboxypentyl)oxy]-1-cyclohexyl-2-phenyl-benzimidazole is obtained as a solid.

Flash point 185–188° C.

Sample Compound 15

1-Allyl-5-[(5-(methoxycarbonyl)pentyl)oxy]-2-phenyl-benzimidazole a) 3,4-Dinitrophenol is alkylated according to general operating instructions 2 with 6-bromo-hexanoic acid-methyl ester. 6-[3,4-Dinitro-phenoxy]hexanoic acid methyl ester is obtained as a yellow oil.
b) 6-[3,4-Dinitrophenoxy]hexanoic acid methyl ester is hydrogenated according to general operating instructions 3. In this case, 6-(3,4-diamino-phenoxy)hexanoic acid methyl ester is obtained as a black oil.
c) 6-(3,4-Diamino-phenoxy)hexanoic acid methyl ester is reacted with trimethylorthobenzoate according to general operating instructions 10 to form benzimidazole. 6-[(5-(Methoxycarbonyl)pentyl)oxy]-2-phenyl-1H-benzimidazole is obtained as a solid.
d) 6-[(5-(Methoxycarbonyl)pentyl)oxy]-2-phenyl-1H-benzifnidazole is reacted according to general operating instructions 6 with allyl bromide. After HPLC separation, 1-allyl-5-[(5-(methoxycarbonyl)pentyl)oxy]-2-phenyl-benzimidazole is obtained as a white solid.

MS (EI): 378 (molecular ion peak)

Sample Compound 16

1-Allyl-6-[(5-(methoxycarbonyl)pentyl)oxy]-2-phenyl-benzimidazole is produced analogously to sample compound 15.

MS (EI): 378 (molecular ion peak)

Sample Compound 24

1-Cyclohexyl-6-[(5-((3-methyl-butyl)-aminocarbonyl)pentyl)oxy]-2-phenyl-benzimidazole 1-Cyclohexyl-6-[(5-(methoxycarbonyl)pentyl)oxy]-2-phenyl-benzimidazole is reacted according to general operating instructions 7 with isoamylamine. 1-Cyclohexyl-6-[(5-((3-methyl-butyl)aminocarbonyl)pentyl)oxy]-2-phenyl-benzimidazole is obtained as a solid.

$^1$H-NMR (CDCl$_3$): δ=0.90 ppm d (J=7.5 Hz, 6H); 1.24–1.45 m (5H); 1.50–2.02 m (12H); 2.20 t (J=7.5 Hz, 2H); 2.20–2.38 m (2H); 3.28 dt (J=7.5, 8 Hz, 2H); 4.03 t (J=7.5 Hz, 2H); 4.25–4.40m (1H); 5.38–5.49 m (1H); 6.90 dd (J=8.2 Hz, 1H); 7.10 d (J=2 Hz, 1H); 7.48–7.55 m (3H); 7.59–7.67 m (2H); 7.68 d (J=8 Hz, 1H).

Example 25

1-Cyclohexyl-2-phenyl-6-[(5-(iso-propylaminocarbonyl)pentyl)oxy]-benzimidazole

1-Cyclohexyl-6-[(5-(methoxycarbonyl)pentyl)oxy]-2-phenyl-benzimidazole is reacted according to general operating instructions 7 with isopropylamine. 1-Cyclohexyl-2-phenyl-6-[(5-(iso-propylamirnocarbonyl)pentyl)oxy]-benzimidazole is obtained as a solid.

$^1$H-NMR (CDCl$_3$): δ=1.12 ppm d (J=7.5 Hz, 6H); 1.24–1.43 m (4H); 1.52–2.00 m (10H); 2.20 t (J=7.5 Hz, 2H); 2.20–2.40 m (2H); 4.04 t (J=7.5 Hz, 2H); 4.10 sp (J=7.5 Hz, 1H); 4.25–4.40 m (1H); 5.25–5.40 m (1H); 6.90 dd (J=8.2 Hz, 1H); 7.11 d (J=2 Hz, 1H); 7.48–7.57 m (3H); 7.59–7.65 m (2H); 7.69 d (J=8 Hz, 1H).

Example 26

1-Cyclohexyl-6-[(5-((3-methoxy-propyl)aminocarbonyl)pentyl)oxy]-2-phenyl-benzimidazole 1-Cyclohexyl-6-[(5-(methoxycarbonyl)pentyl)oxy]-2-phenyl-benzimidazole is reacted according to general operating instructions 7 with 3-methoxypropylamine. 1-Cyclohexyl-6-[(5-((3-methoxy-propyl)aminocarbonyl)pentyl)oxy]-2-phenyl-benzimidazole is obtained as a solid.

$^1$H-NMR (CDCl$_3$): δ=1.25–1.40 ppm m (4H); 1.52–2.00 m (12H); 2.22 t (J=7.5 Hz, 2H); 2.25–2.40 m (2H); 3.35 s (3H); 3.40 dt (J=8.8 Hz, 2H); 3.49 t (J=7.5 Hz, 2H); 4.02 t (J=7.5 Hz, 2H); 4.24–4.40 m (1H); 5.98–6.10 m (1H); 6.90 dd (J=8.2 Hz, 1H); 7.10 d (J=2 Hz, 1H); 7.47–7.56 m (3H); 7.58–7.65 m (2H); 7.70 d (J=8 Hz, 1H).

Example 27

1-Cyclohexyl-6-[(5-((N,N-dimethylamino)carbonyl)pentyl)oxy]-2-phenyl-benzimidazole 1-Cyclohexyl-6-[(5-(methoxycarbonyl)pentyl)oxy]-2-phenyl-benzimidazole is reacted according to general operating instructions 7 with dimethylamine hydrochloride. 1-Cyclo-hexyl-6-[(5-((N,N-dimethylamino)carbonyl)pentyl)oxy]-2-phenyl-benzimidazole is obtained as a solid.

$^1$H-NMR (CDCl$_3$): δ=1.22–1.43 ppm m (4H); 1.54–2.00 m (10H); 2.22–2.45 m (2H); 2.38 t (J=7.5 Hz, 2H); 2.95 s (3H); 3.03 s (3H); 4.05 t (J=7.5 Hz, 2H); 4.25–4.40 m (1H); 6.90 dd (J=8.2 Hz, 1H); 7.10 d (J=2 Hz, 1H); 7.45–7.56 m (3H); 7.57–7.64 m (2H); 7.68 d (J=8 Hz, 1H).

Sample Compound 28

1-Cyclohexylmethyl-6-[(5-(methoxycarbonyl)pentyl)oxy]-2-phenyl-benzimidazole is obtained by reaction of 6-[(5-methoxycarbonyl)pentyl)oxy]-2-phenyl-1H-benzimidazole with cyclohexylmethyl bromide according to general operating instructions 6.

MS (EI): 434 (molecular ion peak)

Sample Compound 29

1-Cyclohexylmethyl-5-[(5-(methoxycarbonyl)pentyl)oxy]-2-phenyl-benzimidazole is obtained by reaction of 6-[(5-(methoxycarbonyl)pentyl)oxy]-2-phenyl-1H-benzimidazole with cyclohexylmethyl bromide according to general operating instructions 6.

MS (EI): 434 (molecular ion peak)

Sample Compound 41

6-[(5-Methoxycarbonyl)pentyl)oxy]-1-(3-methoxypropyl)-2-(pyrid-3-yl)-benzimidazole 6-[3-(3-Methoxypropylamino)-4-amino-phenoxy] hexanoic acid methyl ester is reacted with 3-pyridiyl-carbaldehyde according to general operating instructions 4 to form benzimidazole. 6-[(5-(Methoxycarbonyl)pentyl)oxy]-1-(3-methoxy-propyl)-2-(pyrid-3-yl)-benzimidazole is obtained as a yellow solid.

MS (EI): 411 (molecular ion peak)

The following sample compounds 34, 39, 42, 43, 44, 45 and 47 are obtained with the corresponding carbaldehydes analogously to Example 41:

Sample Compound 34

2-(4-Cyano-phenyl)-6-[(5-(methoxycarbonyl)pentyl)oxy]-1-(3-methoxypropyl)-benzimidazole MS (EI): 435 (molecular ion peak)

Sample Compound 39

2-(4-tert-Butyl-phenyl)-6-[(5-(methoxycarbonyl)pentyl)oxy]-1-(3-methoxy-propyl)-benzimidazole MS (EI): 466 (molecular ion peak)

Sample Compound 42

6-[(5-(Methoxycarbonyl)pentyl)oxy]-1-(3-methoxypropyl)-2-(pyrid-4-yl)-benzimidazole MS (EI): 411 (molecular ion peak)

Sample Compound 43

6-[(5-(Methoxycarbonyl)pentyl)oxy]-1-(3-methoxypropyl)-2-(thien-2-yl)-benzimidazole MS (EI): 416 (molecular ion peak)

Sample Compound 44

6-[(5-(Methoxycarbonyl)pentyl)oxy]-1-(3-methoxypropyl)-2-(thien-3-yl)-benzimidazole MS (EI): 416 (molecular ion peak)

Sample Compound 45

2-(Indol-3-yl)-6-[(5-(methoxycarbonyl)pentyl)oxy]-1-(3-methoxy-propyl)-benzimidazole MS (EI): 449 (molecular ion peak)

Sample Compound 47

2-(Fur-3-yl)-6-[(5-(methoxycarbonyl)pentyl)oxy]-1-(3-methoxy-propyl)-benzimidazole MS (EI): 400 (molecular ion peak)

Sample Compound 60

6-[(5-Carboxy-pentyl)oxy]-1-(3-methoxy-propyl)-2-(pyrid-3-yl)-benzimidazole

6-[(5-(Methoxycarbonyl)pentyl)oxy]-1-(3-methoxy-propyl)-2-(pyrid-3-yl)-benzimidazole is saponified according to general operating instructions 5. 6-[(5-Carboxy-pentyl)oxy]-1-(3-methoxy-propyl)-2-(pyrid-3-yl)-benzimidazole is obtained as a yellow solid.

MS (EI): 397 (molecular ion peak)

The following examples 53, 58, 61, 62, 63, 64 and 65 are obtained from the corresponding methyl esters analogously to Example 60:

Sample Compound 53

6-[(5-Carboxy-pentyl)oxy]-2-(4-cyano-phenyl)-1-(3-methoxy-propyl)-benzimidazole

MS (EI): 421 (molecular ion peak)

Sample Compound 58

2-(4-tert-Butyl-phenyl)-6-[(5-carboxy-pentyl)oxy]-1-(3-methoxy-propyl)-benzimidazole MS (EI): 452 (molecular ion peak)

Sample Compound 61

6-[(5-Carboxy-pentyl)oxy]-1-(3-methoxy-propyl)-2-(pyrid-4-yl)-benzimidazole

MS (EI): 397 (molecular ion peak)

Sample Compound 62

6-[(5-Carboxy-pentyl)oxy]-1-(3-methoxy-propyl)-2-(thien-2-yl)-benzimidazole

MS (EI): 402 (molecular ion peak)

Sample Compound 63

6-[(5-Carboxy-pentyl)oxy]-1-(3-methoxy-propyl)-2-(thien-3-yl)-benzimidazole

MS (EI): 402 (molecular ion peak)

Sample Compound 64

2-(Indol-3-yl)-6-[(5-carboxy-pentyl)oxy]-1-(3-methoxy-propyl)-benzimidazole

MS (EI): 435 (molecular ion peak)

Sample Compound 65

6-[(5-Carboxy-pentyl)oxy]-2-(fur-3-yl)-1-(3-methoxy-propyl)-benzimidazole

MS (EI): 386 (molecular ion peak)

Sample Compound 79

2-(4-Cyano-phenyl)-1-(3-methoxy-propyl)-6-[(5-((3-methoxy-propyl)aminocarbonyl)pentyl)oxy]-benzimidazole 2-(4-Cyano-phenyl)-6-[(5-(methoxycarbonyl)pentyl)oxy]-1-(3-methoxypropyl)-benzimidazole is reacted with 3-methoxypropylamine according to general operating instructions 7. 2-(4-Cyano-phenyl)-1-(3-methoxy-propyl)-6-[(5-((3-methoxy-propyl)aminocarbonyl)-pentyl)oxy]-benzimidazole is obtained as a yellow solid.

MS (EI): 492 (molecular ion peak)

Sample Compound 84

2-(4-tert-Butyl-phenyl)-1-(3-methoxy-propyl)-6-[(5-((3-methoxy-propyl)aminocarbonyl)-pentyl)oxy]-benzimidazole 2-(4-tert-Butyl-phenyl)-6-[(5-(methoxycarbonyl)pentyl)oxy]-1-(3-methoxy-propyl)-benzimidazole is reacted with 3-methoxypropylamine according to general operating instructions 7. 2-(4-tert-Butyl-phenyl)-1-(3-methoxy-propyl)-6-[(5-((3-methoxy-propyl)amino-carbonyl)-pentyl)oxy]-benzimidazole is obtained as a yellow solid.

MS (EI): 523 (molecular ion peak)

Sample Compound 87

6-[(5-(Methoxycarbonyl)pentyl)oxy]-2-(4-methoxy-phenyl)-1-[3-morpholin-4-yl-propyl]-benzimidazole a) 3-Fluoro-4-nitrophenol is reacted with 3,3-diethoxypropylamine according to general operating instructions 1. 3-(3,3-Diethoxypropyl)-4-nitrophenol is obtained as a red oil, which is further processed in a crude form.

b) 3-(3,3-Diethoxypropyl)-4-nitrophenol is alkylated with 6-bromo-hexanoic acid methyl ester according to general operating instructions 2. 6-[3-(3,3-diethoxypropyl)-4-nitro-phenoxy]hexanoic acid methyl ester is obtained as a yellow oil.

c) 6-[3-(3,3-Diethoxypropyl)-4-nitro-phenoxy]hexanoic acid methyl ester is hydrogenated according to general operating instructions 3. In this case, 6-[3-(3,3-diethoxypropyl)-4-amino-phenoxy]hexanoic acid methyl ester is obtained as a black oil.

d) 6-[3-(3,3-Diethoxypropyl)-4-amino-phenoxy]hexanoic acid methyl ester is reacted with 4-methoxybenzaldehyde according to general operating instructions 4 to form benzimidazole. 1-(3,3-Diethoxy-propyl)-6-[(5-(methoxy-carbonyl)pentyl)oxy]-2-(4-methoxy-phenyl)-benzimidazole is obtained as a brown oil.

e) 1-(3,3-Diethoxy-propyl)-6-[(5-(methoxycarbonyl)pentyl)oxy]-2-(4-methoxy-phenyl)-benzimidazole (13 mmol) is dissolved in 600 ml of acetone. 33 ml of 6N hydrochloric acid is added in drops to this at room temperature. It is allowed to stir for one hour, neutralized with sodium bicarbonate solution, and the acetone is removed in a vacuum. The residue is extracted with ethyl acetate, washed with brine, and dried on sodium sulfate. It is filtered off, then concentrated by evaporation, and 6-[(5-(methoxycarbonyl)pentyl)oxy]-2-(4-methoxy-phenyl)-1-(3-oxo-propyl)-benzimidazole is obtained.

f) 6-[(5-(Methoxycarbonyl)pentyl)oxy]-2-(4-methoxy-phenyl)-1-(3-oxo-propyl)-benzimidazole is reacted with morpholine according to general operating instructions 8.

6-[(5-(Methoxycarbonyl)pentyl)oxy]-2-(4-methoxyphenyl)-1-[3-morpholin-4-yl-propyl]-benzimidazole is obtained as a yellow oil.

MS (EI): 495 (molecular ion peak)

Sample Compound 96

6-[(5-(Methoxycarbonyl)pentyl)oxy]-2-(4-methoxyphenyl)-1-[3-(4-phenyl-piperazin-1-yl)-propyl]-benzimidazole 6-[(5-(Methoxycarbonyl)pentyl)oxy]-2-(4-methoxyphenyl)-1-(3-oxo-propyl)-benzimidazole is reacted with N-phenyl-piperazine according to general operating instructions 8. 6-[(5-(Methoxycarbonyl)pentyl)oxy]-2-(4-methoxy-phenyl)-1-[3-(4-phenyl-piperazin-1-yl)-propyl]-benzimidazole is obtained as a yellow oil.

MS (EI): 570 (molecular ion peak)

The following sample compounds 91, 95, 98 and 102 were produced with the corresponding amines analogously to Example 96:

Sample Compound 91

1-(3-(N,N-Diethylamino)propyl)-6-[(5-(methoxycarbonyl)pentyl)oxy]-2-(4-methoxyphenyl)-benzimidazole MS (EI): 481 (molecular ion peak)

Sample Compound 95

6-[(5-(Methoxycarbonyl)pentyl)oxy]-2-(4-methoxyphenyl)-1-[3-(4-pyrid-2-yl-piperazin-1-yl)-propyl]-benzimidazole MS (EI): 571 (molecular ion peak)

Sample Compound 98

6-[(5-(Methoxycarbonyl)pentyl)oxy]-2-(4-methoxyphenyl)-1-[3-(4-pyrimid-2-yl-piperazin-1-yl)-propyl]-benzimidazole MS (EI): 572 (molecular ion peak)

Sample Compound 102

1-[3-(4-(2-Hydroxyethyl)piperazin-1-yl)propyl]-6-[(5-(methoxycarbonyl)pentyl)oxy]-2-(4-methoxyphenyl)-benzimidazole MS (EI): 538 (molecular ion peak)

Sample Compound 104

6-[(5-(Methoxycarbonyl)pentyl)oxy]-2-(4-methoxyphenyl)-1-[3-(N-methyl-N-(methyl-carbonyl)amino)propyl]-benzimidazole a) 6-[(5-(Methoxycarbonyl)pentyl)oxy]-2-(4-methoxyphenyl)-1-(3-oxo-propyl)-benzimidazole is reacted with aqueous methylamine solution according to general operating instructions 8. 6-[(5-(Methoxcarbonyl)pentyl)oxy]-2-(4-methoxy-phenyl)-1-[3-(N-methyl-amino)propyl]-benzimidazole is obtained as a yellow oil.
b) 6-[(5-(Methoxycarbonyl)pentyl)oxy]-2-(4-methoxyphenyl)-1-[-3-(N-methyl-amino)propyl]-benzimnidazole is reacted with acetic anhydride according to general operating instructions 9. 6-[(5-(Methoxycarbonyl)pentyl)oxy]-2-(4-methoxy-phenyl)-1-[3-(N-methyl-N-(methylcarbonyl)amino)propyl]-benzimidazole is obtained as a yellow oil.

MS (EI): 481 (molecular ion peak)

The following examples 105, 106, 107, 108, 110 and 112 were produced with the corresponding amines analogously to Example 22:

Sample Compound 105

6-[(5-(Methoxycarbonyl)pentyl)oxy]-2-(4-methoxyphenyl)-1-(3-[N-methyl-N-(trifluoro-methylcarbonyl)amino)propyl]-benzimidazole MS (EI): 535 (molecular ion peak)

Sample Compound 106

6-[(5-(Methoxycarbonyl)pentyl)oxy]-2-(4-methoxyphenyl)-1-(3-[N-methyl-N-(methyl-sulfonyl)amino) propyl]-benzimidazole MS (EI): 517 (molecular ion peak)

Sample Compound 107

6-[(5-(Methoxycarbonyl)pentyl)oxy]-2-(4-methoxyphenyl)-1-[3-(N-methyl-N-((2-methylthio-ethyl)carbonyl)amino)propyl]-benzimidazole MS (EI). 541 (molecular ion peak)

Sample Compound 108

6-[(5-(Methoxycarbonyl)pentyl)oxy]-2-(4-methoxyphenyl)-1-(3-[N-methyl-N-(trimethylmethylcarbonyl)amino)propyl]-benzimidazole MS (EI): 523 (molecular ion peak)

Sample Compound 110

6-[(5-(Methoxycarbonyl)pentyl)oxy]-2-(4-methoxyphenyl)-1-[3-(N-methyl-N-(fur-2-yl-carbonyl)amino)propyl]-benzimidazole MS (EI): 533 (molecular ion peak)

Sample Compound 112

6-[(5-(Methoxycarbonyl)pentyl)oxy]-2-(4-methoxyphenyl)-1-[3-(N-methyl-N-(methoxymethylcarbonyl)amino)propyl]-benzimidazole MS (EI): 511 (molecular ion peak)

Example 114

Biological Testing

Inhibition of Microglia Activation

For in vitro production of Aβ-activated microglia, primary rat microglia are incubated with synthetic Aβ peptide:

To simulate Aβ deposits, synthetic Aβ peptide is dried on 96-hole tissue culture plates. A peptide stock solution of 2 mg/ml of $H_2O$ 1:50 in $H_2O$, is diluted in this. To coat the 96-hole plates, 30 μL of this dilute peptide solution/hole is used and dried overnight at room temperature.

Primary rat microglia are harvested from mixed glia cultures, which were obtained from P3 rat brains. For the production of mixed glia cultures, the brains are removed from 3-day-old rats and meninges are removed therefrom. The isolation of cells is achieved by trypsinization (0.25% trypsin solution, 15 minutes 37° C.)). After undigested tissue fragments are separated with the aid of a 40 □m nylon mesh, the isolated cells are centrifuged off (800 rpm/10 minutes). The cell pellet is resuspended in culture medium and moved into 100 ml tissue culture flasks (1 brain/tissue culture flask). The cells are cultivated over a period of 5 to 7 days in Dulbeccos Modified Eagle Medium (DMEM, with glutamine), supplemented with penicillin (50 U/mil), streptomycin (40 µg/ml) and 10% (v/v) fetal calf serum (FCS) at 37° C. and 5% CO2. During this incubation, an adhesive cellular film that mainly consists of astrocytes is formed. Microglia proliferate as non-adhesive or slightly adhesive cells on the latter and are harvested via shaking incubation (420 rpm, 1 hour).

To activate the microglia by Aβ peptide, $2.5 \times 10^4$ microglia/hole is grown on the A□-coated tissue culture plates and incubated over a period of 7 days in DMEM (with glutamine), supplemented with penicillin (50 U/ml), streptomycin (40 µg/ml) and 10% (v/v) fetal calf serum (FCS) at 37° C. and 5% CO2. On day 5, a compound according to the invention is added at various concentrations (0.1, 0.3, 1.3, and 10 µM).

To quantify the microglia reactivity, the metabolic activity is measured on cultivation day 7 via the reduction of MTS (3-(4,5-dimethylthiazol-2-yl)-5-(3carboxymethoxyphenyl)-2-(sulfophenyl)-2H-tetrazolium), Owen's reagent, Baltrop, J. A. et al., *Bioorg. & Med. Chem. Lett.*, 1, 6111 (1991)). The percent of inhibition relates to a control that is treated only with DMSO. The compounds according to the invention inhibit the microglia activation.

Examples of the inhibition of the microglia activation according to the above-described test process:

| Test Compound | IC50 in the Microglia Inhibition Test |
|---|---|
| 6-[(5-(Methoxycarbonyl)pentyl)oxy]-1-(3-methoxy-n-propyl)-2-phenyl-benzimidazole | 0.65 |
| 6-[(5-(Methoxycarbonyl)pentyl)oxy]-2-(4-methoxy-phenyl)-1-[3-(N-methyl-N-(methylcarbonyl)amino)propyl]-benzimidazole | 0.39 |

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. Benzimidazole derivatives with general formula I:

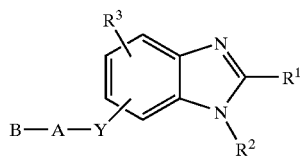

(I)

in which
R$^1$ stands for an aryl group, whereby the aryl group can be substituted with up to three radicals, independently of one another, selected from the group consisting of:

F, Cl, Br, C(NH)NH$_2$, C(NH)NHR$^4$, C(NH)NR$^4$R$^{4'}$, C(NR$^4$)NH$_2$, C(NR$^4$)NHR$^{4'}$, C(NR$^4$)NR$^4$R$^{4'}$,

X—OH, X—OR$^4$, X—OCOR$^4$, X—OCONHR$^4$, X—COR$^4$, X—C(NOH)R$^4$,

X—CN, X—COOH, X—COOR$^4$, X—CONH$_2$, X—CONR$^4$R$^{4'}$, X—CONHR$^4$,

X—CONHOH, X—SR$^4$, X—SOR$^4$, X—SO$_2$R$^4$, SO$_2$NH$_2$,

SO$_2$NHR$^4$, SO$_2$NR$^4$R$^{4'}$, NO$_2$, X—NH$_2$, X—NHR$^4$, X—NR$^4$R$^{4'}$, X—NHSO$_2$R$^4$,

X—NR$^4$SO$_2$R$^{4'}$,

X—NHCOR$^4$, X—NHCOOR$^4$, X—NHCONHR$^4$ and R$^4$, whereby X is a bond, CH$_2$, (CH$_2$)$_2$ or CH(CH$_3$), and radicals R$^4$ and R$^{4'}$ are selected independently of one another according to the meanings that are further indicated below, whereby two substituents at R$^1$, if they are in ortho-position to one another, are linked to one another in such a way that they jointly form a methanediylbisoxy, ethane-1,2-diylbisoxy, propane-1,3-diyl or butane-1,4-diyl group, R$^2$ stands for a radical that is C$_{1-6}$-alkyl or C$_{3-6}$-alkenyl, whereby the alkyl and alkenyl radicals can be substituted with up to two radicals, selected from the group consisting of C$_{0-2}$-alkanediyl-OH, C$_{0-2}$-alkanediyl-OR$^7$, C$_{0-2}$-alkanediyl-NH$_2$, C$_{0-2}$-alkanediyl-NHR$^7$, C$_{0-2}$-alkanediyl-NR$^7$R$^{7'}$, C$_{0-2}$-alkanediyl-NHCOR$^7$, C$_{0-2}$-alkanediyl-NR$^7$COR$^{7'}$, C$_{0-2}$-alkanediyl-NHSO$_2$R$^7$, C$_{0-2}$-alkanediyl-NR$^7$SO$_2$R$^{7'}$, C$_{0-2}$-alkanediyl-CO$_2$H, C$_{0-2}$-alkanediyl-CO$_2$R$^7$, C$_{0-2}$-alkanediyl-CONH$_2$, C$_{0-2}$-alkanediyl-CONHR$^7$, C$_{0-2}$-alkanediyl-CONR$^7$R$^{7'}$, phenyl and five- and six-membered heteroaryl radicals, whereby the heteroaryl radical contains one or two heteroatoms, selected from the group consisting of N, S and O, and whereby R$^7$ and R$^{7'}$, independently of one another, in each case stand for R$^4$ or R$^6$, whereby R$^4$ and R$^6$ have the meanings that are indicated below, whereby also the phenyl radical and/or the heteroaryl radical can be substituted with up to two radicals, selected from the group consisting of F, Cl, Br, CH$_3$, C$_2$H$_5$, OH, OCH$_3$, OC$_2$H$_5$, NO$_2$, N(CH$_3$)$_2$, CF$_3$, C$_2$F$_5$ and SO$_2$NH$_2$ and/or can also carry an anellated methanediylbisoxy group or an ethane-1,2 diylbisoxy group, whereby also an H atom can be exchanged for a heterocyclic radical that is pyrrolidine, such that a bond to a first N atom of the heterocyclic radical is formed, whereby the piperazine radical can be substituted on a second N atom also with R$^7$, COR$^7$ or SO$_2$R$^7$, whereby R$^7$ and R$^{7'}$, independently of one another, in each case stand for R$^4$ or R$^6$, and whereby R$^4$ and R$^6$ have the meanings that are indicated below, R$^3$ stands for one or two substituents, which can be selected independently of one another, selected from the group consisting of:
hydrogen,
F, Cl, Br,
OH, OR$^4$, OCOR$^4$, OCONHR$^4$,
COR$^4$,
CN, COOH, COOR$^4$, CONH$_2$, CONHR$^4$, CONR$^4$R$^{4'}$, CONHOH,
CONHOR$^4$,
SR$^4$, SOR$^4$, SO$_2$R$^4$, SO$_2$NH$_2$, SO$_2$NHR$^4$, SO$_2$NR$^4$R$^{4'}$, NO$_2$, NH$_2$, NHR$^4$, NR$^4$R$^{4\prime}$,
NHSO$_2$R$^4$, NR$^4$SO$_2$R$^{4\prime}$, NHSO$_2$R$^6$, NR$^4$SO$_2$R$^6$,
NHCOR$^4$, NHCOOR$^4$, NHCONHR$^4$ and R$^4$,
whereby R$^4$, R$^{4\prime}$ and R$^6$, independently of one another, are selected according to the meanings that are further indicated below, A stands for a group that is selected from the group consisting of C$_{1-10}$-alkanediyl, C$_{2-10}$-alkenediyl, C$_{2-10}$-alkinediyl and (C$_{0-3}$-alkanediyl-C$_{3-7}$-cycloalkanediyl-C$_{0-3}$-alkanediyl),
whereby if the cycloalkyl ring can be five-membered, a ring member in the cycloalkyl ring is a ring-N or a ring-O or if the cycloalkyl ring is six- or seven-membered, one or two ring members in the cycloalkyl ring can be ring-N and/or ring-O atoms in each case, whereby the ring-N atoms can be substituted with C$_{1-3}$-alkyl or C$_{1-3}$-alkanoyl,
whereby also in the aliphatic chains of C$_{1-10}$-alkanediyl, C$_{2-10}$-alkenediyl, C$_{2-10}$-alkinediyl and (C$_{0-3}$-alkanediyl-C$_{3-7}$-cycloalkanediyl-C$_{0-3}$-alkanediyl) groups, a C atom can be exchanged for O, NH, N—C$_{1-3}$-alkyl or N—C$_{1-3}$-alkanoyl, whereby at least one of the alkyl groups and/or cycloalkyl groups can be substituted with a radical that is selected from the group consisting of =O, OH, O—C$_{1-3}$-alkyl, NH$_2$, NH—C$_{1-3}$-alkyl, NH—C$_{1-3}$-alkanoyl, N(C$_{1-3}$-alkyl)$_2$ and N(C$_{1-3}$-alkyl)(C$_{1-3}$-alkanoyl), B stands for a radical that is selected from the group consisting of COOH, COOR$^5$, CONH$_2$, CONHNH$_2$, CONHR$^5$, CONR$^5$R$^{5\prime}$, CONHOH, CONHOR$^5$ and tetrazolyl,
whereby B is bonded to a C atom of group A, and
whereby radicals R$^5$ and R$^{5\prime}$ are selected independently of one another and have the meanings that are further indicated below, Y stands for a group that is selected from the group consisting of O, NH, NR$^4$, NCOR$^4$, NSO$_2$R$^4$ and NSO$_2$R$^6$,
whereby R$^4$ and R$^6$ have the meanings that are further indicated below, R$^4$ and R$^{4\prime}$ in each case stand for a radical that is selected from the consisting of CF$_3$, C$_2$F$_5$, C$_{1-4}$-alkyl, C$_{2-4}$-alkenyl, C$_{2-3}$-alkinyl and (C$_{0-3}$-alkanediyl-C$_{3-7}$-cycloalkyl),
whereby the alkyl radicals can be substituted with a radical that is selected from the group consisting of OH, OCH$_3$ and SCH$_3$,
and whereby if the cycloalkyl ring is five-membered, a ring member in the cycloalkyl ring can be a ring-N or a ring-O, and if the cycloalkyl ring is six- or seven-membered, one or two ring members in the cycloalkyl ring can be ring-N and/or ring-O atoms in each case, whereby the ring-N atoms can be substituted with C$_{1-3}$-alkyl or C$_{1-3}$-alkanoyl, R$^5$ and R$^{5\prime}$ in each case stand for a radical that is selected from the group consisting of C$_{1-6}$-alkyl, C$_{2-6}$-alkenyl and C$_{2-6}$-alkinyl, whereby a C atom in at least one of the radicals can be exchanged for O, S, SO, SO$_2$, NH, N—C$_{1-3}$-alkyl or N—C$_{1-3}$-alkanoyl, also for (C$_{0-3}$-alkanediyl-C$_{3-7}$-cycloalkyl), whereby if the cycloalkyl ring is five-membered, a ring member in the cycloalkyl ring can be a ring-N or a ring-O or if the cycloalkyl ring is six- or seven-membered, one or two ring members in the cycloalkyl ring in each case can be ring-N and/or ring-O atoms, whereby the ring-N atoms can be substituted with at least one radical that is selected from the group consisting of C$_{1-3}$-alkyl and C$_{1-3}$-alkanoyl, and also stand for (C$_{0-3}$-alkanediyl-aryl) and (C$_{0-3}$-alkanediyl-heteroaryl),
whereby the heteroaryl group is five- or six-membered and can contain one or two heteroatoms, selected from the group consisting of N, S and O,
whereby at least one of the above-mentioned alkyl and cycloalkyl radicals can be substituted with up to two radicals, selected from the group consisting of CF$_3$, C$_2$F$_5$, OH, O—C$_{1-3}$-alkyl, NH$_2$, NH—C$_{1-3}$-alkyl, NH—C$_{1-3}$-alkanoyl, N(C$_{1-3}$-alkyl)$_2$, N(C$_{1-3}$-alkyl)(C$_{1-3}$-alkanoyl), COOH, CONH$_2$ and COO—C$_{1-3}$-alkyl, and at least one of the aryl and heteroaryl groups can be substituted with up to two radicals, selected from the group consisting of F, Cl, Br, CH$_3$, C$_2$H$_5$, OH, OCH$_3$, OC$_2$H$_5$, NO$_2$, N(CH$_3$)$_2$, CF$_3$, C$_2$F$_5$ and SO$_2$NH$_2$ and/or at least one of the alkyl, cycloalkyl, aryl and/or heteroaryl radicals can carry an anellated methanediylbisoxy group or ethane-1,2-diylbisoxy group,
or R$^5$ and R$^{5\prime}$ together with the amide-N atom of B form a five- to seven-membered, saturated or unsaturated heterocyclic ring, whereby the heterocyclic ring can contain another N or O or S atom of B, and the heterocyclic ring can be substituted with C$_{1-4}$-alkyl, (C$_{0-2}$-alkanediyl-C$_{1-4}$-alkoxy), C$_{1-4}$-alkoxycarbonyl, aminocarbonyl and aryl, R$^6$ stands for a radical that is selected from the group consisting of (C$_{0-3}$-alkanediyl-aryl) and (C$_{0-3}$-alkanediyl-heteroaryl), whereby the heteroaryl group is five- or six-membered and contains one or two heteroatoms, selected from the group consisting of N, S and O,
whereby at least one of the aryl and heteroaryl groups can be substituted with up to two radicals in each case, selected from the group consisting of F, Cl, Br, CH$_3$, C$_2$H$_5$, OH, OCH$_3$, OC$_2$H$_5$, NO$_2$, N(CH$_3$)$_2$, CF$_3$, C$_2$F$_5$, and SO$_2$NH$_2$ and/or at least one of the aryl or heteroaryl groups can also carry an anellated methanediylbisoxy group or ethane-1,2-diylbisoxy group.

2. Benzimidazole derivatives according to claim 1, characterized in that derivatives are excluded in which R$^2$ is methyl and R$^1$ is substituted with CN or C(NH)NH$_2$, if Y stands for NR$^4$ and B stands for COOH or COOR$^5$.

3. Benzimidazole derivatives according to claim 1, wherein R$^3$ is a radical that is selected from the group consisting of hydrogen, F, Cl, Br, CH$_3$, C$_2$H$_5$, CF$_3$, C$_2$F$_5$, OH, OR$^4$, NHSO$_2$R$^6$ and NHCOR$^4$.

4. Benzimidazole derivatives according to claim 1, wherein B stands for a radical that is selected from the group consisting of COOH, COOR$^5$, CONH$_2$, CONHR$^5$ and CONR$^5$R$^{5\prime}$ whereby radicals R$^5$ and R$^{5\prime}$ are selected independently of one another.

5. Benzimidazole derivatives according to claim 1, whereby Y stands for O.

6. Benzimidazole derivatives according to claim 1, wherein R$^5$ and R$^{5\prime}$ in each case stand for a radical that is selected from the group consisting of C$_{1-6}$-alkyl, C$_{2-6}$-alkenyl, C$_{2-6}$-alkinyl, (C$_{0-3}$-alkanediyl-C$_{3-7}$-cycloalkyl), (C$_{0-3}$-alkanediyl-phenyl) and (C$_{0-3}$-alkanediyl-heteroaryl), whereby the heteroaryl ring is five- or six-membered and contains one or two heteroatoms, selected from the group consisting of N, S and O, whereby all previously mentioned alkyl and cycloalkyl radicals can be substituted with a radical that is selected from the group consisting of CF$_3$, C$_2$F$_5$, OH, O—C$_{1-3}$-alkyl, NH$_2$, NH—C$_{1-3}$-alkyl, NH—C$_{1-}$ 3-alkanoyl, $N(C_{1-3}\text{-alkyl})_2$, $N(C_{1-3}\text{-alkyl})(C_{1-3}\text{-alkanoyl})$, COOH, $CONH_2$ and COO—$C_{1-3}$-alkyl, and all previously mentioned phenyl and heteroaryl groups can be substituted with up to two radicals, selected from the group consisting of F, Cl, Br, $CH_3$, $C_2H_5$, OH, $OCH_3$, $OC_2H_5$, $NO_2$, $N(CH_3)_2$, $CF_3$, $C_2F_5$ and $SO_2NH_2$ and/or also can carry an anellated methanediylbisoxy group or ethane-1,2-diylbisoxy group, or $R^5$ and $R^{5'}$ together with the amide-N atom of B form a five- to seven-membered, saturated or unsaturated heterocyclic ring that can contain another N or O or S atom, and that can be substituted with $C_{1-4}$-alkyl, ($C_{0-2}$-alkanediyl-$C_{1-4}$-alkoxy), $C_{1-4}$-alkoxycarbonyl, aminocarbonyl or phenyl.

7. Benzimidazole derivatives according to claim 1, wherein $R^6$ stands for a phenyl or heteroaryl group,
whereby the heteroaryl group is five- or six-membered and contains one or two heteroatoms, selected from the group consisting of N, S and O, and whereby the phenyl and heteroaryl groups can be substituted with up to two radicals, selected from the group consisting of F, Cl, Br, $CH_3$, $C_2H_5$, OH, $OCH_3$, $OC_2H_5$, $NO_2$, $N(CH_3)_2$, $CF_3$, $C_2F_5$ and $SO_2NH_2$, and/or also can carry an anellated methanediylbisoxy group or ethane-1,2-diylbisoxy group.

8. Benzimidazoles according to claim 1, wherein $R^3$ is hydrogen.

9. Benzimidazole derivatives according to claim 1, wherein
$R^1$ is a phenyl, group, which can be substituted with up to two of the following radicals, independently of one another, selected from the group that consisting of:
F, Cl, Br,
$C(NH)NH_2$, $C(NH)NHR^4$, $C(NH)NR^4R^{4'}$, $C(NR^4)NH_2$, $C(NR^4)NHR^{4'}$,
$C(NR^4)NR^4R^{4'}$,
OH, $OR^4$, $OCOR^4$, $OCONHR^4$,
$COR^4$, $C(NOH)R^4$,
CN, COOH, $COOR^4$, $CONH_2$, $CONR^4R^{4'}$, $CONHR^4$, CONHOH,
$SR^4$, $SOR^4$, $SO_2R^4$,
$SO_2NH_2$, $SO_2NHR^4$, $SO_2NR^4R^{4'}$,
$NO_2$, $NH_2$, $NHR^4$, $NR^4R^{4'}$, $NHCONHR^4$ and $R^4$.

10. Benzimidazole derivatives according to claim 1, wherein
$R^1$ is a phenyl, group, which
can be substituted with up to two of the following radicals, independently of one another, selected from the group consisting of:
F, Cl, Br,
OH, $OR^4$, $OCOR^4$, $OCONHR^4$,
$COR^4$, $C(NOH)R^4$,
COOH, $COOR^4$, $CONH_2$, $CONR^4R^{4'}$, $CONHR^4$, CONHOH,
$SR^4$, $SOR^4$, $SO_2R^4$,
$SO_2NH_2$, $SO_2NHR^4$, $SO_2NR^4R^{4'}$,
$NO_2$, and
$R^4$,
whereby radicals $R^4$ and $R^{4'}$ are selected independently of one another according to meanings that are further indicated below and whereby two substituents at $R^1$ are linked to one another in such a way that they jointly form a methanediylbisoxy, ethane-1,2-diylbisoxy, propane-1,3-diyl or butane-1,4-diyl group, if they are in ortho-position to one another,
$R^2$ means a radical that is $C_{1-6}$-alkyl, or $C_{3-6}$-alkenyl, whereby the above-mentioned alkyl and alkenyl radicals can be substituted, selected from the group that consisting of —OH, —$OR^7$, —$NH_2$, —$NHR^7$, —$NR^7R^{7'}$, —
$NHCOR^7$,
—$NR^7COR^{7'}$, —$NHSO_2R^7$,
—$NR^7SO_2R^{7'}$, —$CO_2H$, —$CO_2R^7$,
—$CONH_2$, —$CONHR^7$, —$CONR^7R^{7'}$, a saturated heterocyclic radical, selected from the group consisting of piperazine, morpholine, piperidine and pyrrolidine, which is bonded via the N atom, phenyl and a five- or six-membered heteroaryl radical, whereby the heteroaryl radical contains one or two heteroatoms, selected from the group consisting of N, S and O,
whereby also the phenyl radical and the heteroaryl radical can be substituted with up to two radicals, selected from the group consisting of F, Cl, Br, $CH_3$, $C_2H_5$, OH, $OCH_3$, $OC_2H_5$, $NO_2$, $N(CH_3)_2$, $CF_3$, $C_2F_5$ and $SO_2NH_2$ and/or can also carry an anellated methanediylbisoxy group or an ethane-1,2 diylbisoxy group,
whereby the piperazine radical can be substituted on a second nitrogen atom also with $R^7$, $COR^7$ or $SO_2R^7$,
whereby $R^7$ and $R^{7'}$ can be selected independently of one another according to the meanings that are further indicated below,
$R^3$ means hydrogen,
A means straight-chain or branched alkanediyl with up to 6 C atoms,
B means a radical that is selected from the group consisting of COOH, $COOR^5$, $CONH_2$, $CONHR^5$ and $CONR^5R^{5'}$,
in each case bonded to a C atom of group A,
whereby radicals $R^5$ and $R^{5'}$, according to the meanings that are further indicated above, are selected independently of one another,
Y means O,
whereby in the above radicals, radicals $R^4$, $R^{4'}$, $R^5$, $R^{5'}$ and $R^7$ have the following meanings:
$R^4$ and $R^{4'}$, independently of one another, in each case mean a radical that is selected from the group consisting of $CF_3$, $C_2F_5$, $C_{1-4}$-alkyl, $C_{2-4}$-alkenyl, $C_{2-3}$-alkinyl and ($C_{0-3}$-alkanediyl-$C_{3-7}$-cycloalkyl), whereby alkyl radicals optionally can be substituted with a radical that is selected from the group consisting of OH, $OCH_3$ and $SCH_3$,
$R^5$ and $R^{5'}$, independently of one another, in each case mean a radical that is selected from the group consisting of $C_{1-6}$-alkyl, $C_{2-6}$-alkenyl, $C_{2-6}$-alkinyl, ($C_{0-3}$-alkanediyl-$C_{3-7}$-cycloalkyl), ($C_{0-3}$-alkanediyl-phenyl) and ($C_{0-3}$-alkanediyl-heteroaryl), whereby the heteroaryl group is five- or six-membered and contains one or two heteroatoms, selected from the group consisting of N, S and O, whereby all previously mentioned alkyl and cycloalkyl radicals can be substituted with a radical that is selected from the group consisting of $CF_3$, $C_2F_5$, OH, O—$C_{1-3}$-alkyl, $NH_2$, NH—$C_{1-3}$-alkyl, NH—$C_{1-3}$-alkanoyl, $N(C_{1-3}\text{-alkyl})_2$, $N(C_{1-3}\text{-alkyl})(C_{1-3}\text{-alkanoyl})$, COOH, $CONH_2$ and COO—$C_{1-3}$-alkyl, and all previously mentioned phenyl and heteroaryl groups can be substituted with up to two radicals, selected from the group consisting of F, Cl, Br, $CH_3$, $C_2H_5$, OH, $OCH_3$, $OC_2H_5$, $NO_2$, $N(CH_3)_2$, $CF_3$, $C_2F_5$, and $SO_2NH_2$, and/or also can carry an anellated methanediylbisoxy group or ethane-1,2-diylbisoxy group, or $R^5$ and $R^{5'}$ together with the amide-N atom of B form a five- to seven-membered, saturated or unsaturated heterocyclic ring, which can contain another N or O or S atom and which can be substituted with $C_{1-4}$-alkyl, ($C_{0-2}$-alkanediyl-$C_{1-4}$-alkoxy), $C_{1-4}$-aloxycarbonyl, aminocarbonyl or phenyl, $R^7$ and $R^{7'}$, independently of one another, mean $R^4$ or $R^6$, and $R^6$ means a phenyl or heteroaryl group, whereby the heteroaryl group is five- or six-membered and contains one or two heteroatoms, selected from the group consisting of N, S and O, and whereby the phenyl and heteroaryl groups can be substituted with up to two radicals, selected from the group consisting of F, Cl, Br, $CH_3$, $C_2H_5$, OH, $OCH_3$, $OC_2H_5$, $NO_2$, $N(CH_3)_2$, $CF_3$, $C_2F_5$ and $SO_2NH_2$, and/or else can carry an anellated methanediylbisoxy group or ethane-1,2-diylbisoxy group.

11. Benzimidazole derivatives according to claim 1 selected from the group consisting of:

1-Benzyl-6-[(5-(Methoxycarbonyl)pentyl)oxy]-2-phenyl-benzimidazole,
1-Benzyl-2-phenyl-6-[(5-(iso-propyloxycarbonyl)pentyl)oxy]-benzimidazole,
1-Benzyl-6-[(5-carboxy-pentyl)oxy]-2-phenyl-benzimidazole,
6-[(5-(Methoxycarbonyl)pentyl)oxy]-1-methyl-2-phenyl-benzimidazole,
6-[(5-(Methoxycarbonyl)pentyl)oxy]-2-phenyl-1-n-propyl-benzimidazole,
5-[(5-(Methoxycarbonyl)pentyl)oxy]-2-phenyl-1-n-propyl-benzimidazole,
6-[(5-(Methoxycarbonyl)pentyl)oxy]-1-(3-methoxy-n-propyl)-2-phenyl-benzimidazole,
6-[(5-(Methoxycarbonyl)pentyl)oxy]-1-(2-methoxy-ethyl)-2-phenyl-benzimidazole,
6-[(5-Carboxy-pentyl)oxy]-1-(3-methoxy-n-propyl)-2-phenyl-benzimidazole,
6-[(5-Carboxy-pentyl)oxy]-1-(2-methoxy-ethyl)-2-phenyl-benzimidazole,
6-[(5-(Methoxycarbonyl)pentyl)oxy]-2-phenyl-1-iso-propyl-benzimidazole,
6-[(5-Carboxy-pentyl)oxy]-2-phenyl-1-iso-propyl-benzimidazole,
1-Allyl-5-[(5-(methoxycarbonyl)pentyl)oxy]-2-phenyl-benzimidazole,
1-Allyl-6-[(5-(methoxycarbonyl)pentyl)oxy]-2-phenyl-benzimidazole,
1-Allyl-6-[(5-carboxy-pentyl)oxy]-2-phenyl-benzimidazole,
1-Allyl-5-[(5-carboxy-pentyl)oxy]-2-phenyl-benzimidazole,
5-[(5-(Methoxycarbonyl)pentyl)oxy]-2-phenyl-1-(3-phenyl-prop-2-enyl)-benzimidazole,
6-[(5-(Methoxycarbonyl)pentyl)oxy]-2-phenyl-1-(3-phenyl-prop-2-enyl)-benzimidazole,
1-[3-(4-Fluoro-phenyl)-prop-2-enyl]-5-[(5-(methoxycarbonyl)pentyl)oxy]-2-phenyl-benzimidazole,
1-[(Ethoxycarbonyl)methyl]-6-[(5-(methoxycarbonyl)pentyl)oxy]-2-phenyl-benzimidazole,
1-[(Ethoxycarbonyl)methyl]-5-[(5-(methoxycarbonyl)pentyl)oxy]-2-phenyl-benzimidazole,
1-[(N,N-Dimethylamino)carbonylmethyl]-5-[(5-(methoxycarbonyl)pentyl)oxy]-2-phenyl-benzimidazole,
1-[(N,N-Dimethylamino)carbonylmethyl]-6-[(5-(methoxycarbonyl)pentyl)oxy]-2-phenyl-benzimidazole,
6-[(5-(Methoxycarbonyl)pentyl)oxy]-1-(3-methoxypropyl)-2-(4-methyl-phenyl)-benzimidazole,
6-[(5-(Methoxycarbonyl)pentyl)oxy]-1-(3-methoxypropyl)-2-(4-nitro-phenyl)-benzimidazole,
2-(4-Cyano-phenyl)-6-[(5-(methoxycarbonyl)pentyl)oxy]-1-(3-methoxypropyl)-benzimidazole,
2-(4-Fluoro-phenyl)-6-[(5-(methoxycarbonyl)pentyl)oxy]-1-(3-methoxypropyl)-benzimidazole,
6-[(5-(Methoxycarbonyl)pentyl)oxy]-1-(3-methoxy-propyl)-2-(4-trifluoromethyl-phenyl)-benzimidazole,
2-[4-(N,N-Dimethylamino)phenyl]-6-[(5-(methoxycarbonyl)pentyl)oxy]-1-(3-methoxy-propyl)-benzimidazole,
6-[(5-(Methoxycarbonyl)pentyl)oxy]-2-(4-methoxy-phenyl)-1-(3-methoxy-propyl)-benzimidazole,
2-(4-tert-Butyl-phenyl)-6-[(5-(methoxycarbonyl)pentyl)oxy]-1-(3-methoxy-propyl)-benzimidazole,
6-[(5-(Methoxycarbonyl)pentyl)oxy]-1-(3-methoxy-propyl)-2-(4-trifluoromethyloxy-phenyl)-benzimidazole,
1-((N,N-Dimethylamino)carbonylmethyl)-5-[(5-(methoxycarbonyl)pentyl)oxy]-2-phenyl-benzimidazole,
1-((N,N-Diethylamino)carbonylmethyl)-6-[(5-(methoxycarbonyl)pentyl)oxy]-2-phenyl-benzimidazole,
2-(4-Hydroxy-phenyl)-6-[(5-(methoxycarbonyl)pentyl)oxy]-1-(3-methoxy-propyl)-benzimidazole,
6-[(5-Carboxy-pentyl)oxy]-1-(3-methoxy-propyl)-2-(4-nitro-phenyl)-benzimidazole,
6-[(5-Carboxy-pentyl)oxy]-2-(4-cyano-phenyl)-1-(3-methoxy-propyl)-benzimidazole,
6-[(5-Carboxy-pentyl)oxy]-2-(4-fluoro-phenyl)-1-(3-methoxy-propyl)-benzimidazole,
6-[(5-Carboxy-pentyl)oxy]-1-(3-methoxy-propyl)-2-(4-trifluoromethyl-phenyl)-benzimidazole,
6-[(5-Carboxy-pentyl)oxy]-2-(4-(N,N-dimethylamino-phenyl)-1-(3-methoxy-propyl)-benzimidazole,
6-[(5-Carboxy-pentyl)oxy]-2-(4-methoxy-phenyl)-1-(3-methoxy-propyl)-benzimidazole,
2-(4-tert-Butyl-phenyl)-6-[(5-carboxy-pentyl)oxy]-1-(3-methoxy-propyl)-benzimidazole,
6-[(5-Carboxy-pentyl)oxy]-1-(3-methoxy-propyl)-2-(4-trifluoromethyloxy-phenyl)-benzimidazole,
1-Carboxymethyl-6-[(5-carboxy-pentyl)oxy]-2-phenyl-benzimidazole,
1-Carboxymethyl-5-[(5-carboxy-pentyl)oxy]-2-phenyl-benzimidazole,
6-[(5-Carboxy-pentyl)oxy]-2-phenyl-1-(3-phenyl-prop-2-enyl)-benzimidazole
6-[(5-Carboxy-pentyl)oxy]-1-(3-phenyl-prop-2-enyl)-benzimidazole,
5-[(5-Carboxy-pentyl)oxy]-1-(3-phenyl-prop-2-enyl)-benzimidazole,
5-[(5-Carboxy-pentyl)oxy]-1-[((N,N-dimethylamino)carbonyl)methyl]-2-phenyl-benzimidazole,
6-[(5-Carboxy-pentyl)oxy]-1-[((N,N-dimethylamino)carbonyl)methyl]-2-phenyl-benzimidazole,
6-[(5-Carboxy-pentyl)oxy]-1-(3-methoxy-propyl)-2-(4-methyl-phenyl)-benzimidazole, 5-[(5-Carboxy-pentyl)oxy]-1-[((N,N-diethylamino)carbonyl)methyl]-2-phenyl-benzimidazole, 6-[(5-Carboxy-pentyl)oxy]-2-(4-hydroxy-phenyl)-1-(3-methoxy-propyl)-benzimidazole, 1-(3-Methoxy-propyl)-6-[(5-((3-methoxy-propyl)aminocarbonyl)pentyl)oxy]-2-(4-nitro-phenyl)-benzimidazole, 2-(4-Cyano-phenyl)-1-(3-methoxy-propyl)-6-[(5-((3-methoxy-propyl)aminocarbonyl)pentyl)oxy]-benzimidazole, 2-(4-Fluoro-phenyl)-1-(3-methoxy-propyl)-6-[(5-((3-methoxy-propyl)aminocarbonyl)pentyl)oxy]-benzimidazole, 1-(3-Methoxy-propyl)-6-[(5-((3-methoxy-propyl)aminocarbonyl)pentyl)oxy]-2-(4-trifluoromethyl-phenyl)-benzimidazole, 2-(4-(N,N-Dimethylamino)phenyl)-1-(3-methoxy-propyl)-6-[(5-((3-methoxy-propyl)amino-carbonyl)pentyl)oxy]-benzimidazole, 2-(4-Methoxy-phenyl)-1-(3-methoxy-propyl)-6-[(5-((3-methoxy-propyl)aminocarbonyl)pentyl)-oxy]-benzimidazole, 2-(4-tert-Butyl-phenyl)-1-(3-methoxy-propyl)-6-[(5-((3-methoxy-propyl)aminocarbonyl)pentyl)oxy]-benzimidazole, 1-(3-Methoxy-propyl)-6-[(5-((3-methoxy-propyl)aminocarbonyl)pentyl)oxy]-2-(4-trifluoromethyloxy-phenyl)-benzimidazole, 1-(3-Methoxy-propyl)-6-[(5-((3-methoxy-propyl)aminocarbonyl)pentyl)oxy]-2-(4-methyl-phenyl)-benzimidazole, 6-[(5-(Methoxycarbonyl)pentyl)oxy]-2-(4-methoxy-phenyl)-1-[3-morpholin-4-yl-propyl]-benzimidazole, 1-(3-Hydroxy-propyl)-6-[(5-(methoxycarbonyl)pentyl)oxy]-2-(4-methoxy-phenyl)-benzimidazole, 1-(3-Carboxy-ethyl)-6-[(5-(methoxycarbonyl)pentyl)oxy]-2-(4-methoxy-phenyl)-benzimidazole, 1-(3-Methoxycarbonyl-ethyl)-6-[(5-(methoxycarbonyl)pentyl)oxy]-2-(4-methoxy-phenyl)-benzimidazole, 1-(3-(N,N-Diethylamino)propyl)-6-[(5-(methoxycarbonyl)pentyl)oxy]-2-(4-methoxy-phenyl)-benzimidazole, 6-[(5-(Methoxycarbonyl)pentyl)oxy]-2-(4-methoxy-phenyl)-1-[3-pyrrolidin-1-yl-propyl]-benzimidazole, 6-[(5-(Methoxycarbonyl)pentyl)oxy]-2-(4-methoxy-phenyl)-1-[3-piperidin-1-yl-propyl]-benzimidazole, 6-[(5-(Methoxycarbonyl)pentyl)oxy]-1-[3-(N,N-bis(2-methoxyethyl)cyano)-propyl]-2-(4-methoxy-phenyl)-benzimidazole, 6-[(5-(Methoxycarbonyl)pentyl)oxy]-2-(4-methoxy-phenyl)-1-[3-(4-pyrimid-2-yl-piperazin-1-yl)-propyl]-benzimidazole, 6-[(5-(Methoxycarbonyl)pentyl)oxy]-2-(4-methoxy-phenyl)-1-[3-(4-phenyl-piperazin-1-yl)-propyl]-benzimidazole, 6-[(5-(Methoxycarbonyl)pentyl)oxy]-2-(4-methoxy-phenyl)-1-[3-(4-methyl-piperazin-1-yl)-propyl]-benzimidazole, 6-[(5-(Methoxycarbonyl)pentyl)oxy]-2-(4-methoxy-phenyl)-1-[3-(4-pyrimid-2-yl-piperazin-1-yl)-propyl]-benzimidazole, 6-[(5-(Methoxycarbonyl)pentyl)oxy]-2-(4-methoxy-phenyl)-1-[3-(3-imidazol-1-yl-propylamino)propyl]-benzimidazole, 6-[(5-(Methoxycarbonyl)pentyl)oxy]-2-(4-methoxy-phenyl)-1-[3-(4-(fur-2-ylcarbonyl)-piperazin-1-yl)-propyl]-benzimidazole, 6-[(5-(Methoxycarbonyl)pentyl)oxy]-2-(4-methoxy-phenyl)-1-[3-(2-hydroxyl-ethyl)amino-propyl]-benzimidazole, 1-[3-(4-(2-Hydroxyethyl)piperazin-1-yl)propyl]-6-[(5-(methoxycarbonyl)pentyl)oxy]-2-(4-methoxy-phenyl)-benzimidazole, 6-[(5-(Methoxycarbonyl)pentyl)oxy]-2-(4-methoxy-phenyl)-1-[3-imidazol-1-yl-propyl]-benzimidazole, 6-[(5-(Methoxycarbonyl)pentyl)oxy]-2-(4-methoxy-phenyl)-1-[3-(N-methyl-N-(methylcarbonyl)amino)propyl]-benzimidazole, 6-[(5-(Methoxycarbonyl)pentyl)oxy]-2-(4-methoxy-phenyl)-1-(3-[N-methyl-N-(trifluoromethylcarbonyl)amino)propyl]-benzimidazole, 6-[(5-(Methoxycarbonyl)pentyl)oxy]-2-(4-methoxy-phenyl)-1-(3-[N-methyl-N-(methylsulfonyl)amino)propyl]-benzimidazole, 6-[(5-(Methoxycarbonyl)pentyl)oxy]-2-(4-methoxy-phenyl)-1-[3-(N-methyl-N-((2-methylthio-ethyl)carbonyl)amino)propyl]-benzimidazole, 6-[(5-(Methoxycarbonyl)pentyl)oxy]-2-(4-methoxy-phenyl)-1-(3-[N-methyl-N-(trimethylmethylcarbonyl)amino)propyl]-benzimidazole, 6-[(5-(Methoxycarbonyl)pentyl)oxy]-2-(4-methoxy-phenyl)-1-[3-(N-methyl-N-(ethylcarbonyl)amino)propyl]-benzimidazole, 6-[(5-(Methoxycarbonyl)pentyl)oxy]-2-(4-methoxy-phenyl)-1-[3-(N-methyl-N-(fur-2-yl-carbonyl)amino)propyl]-benzimidazole, 6-[(5-(Methoxycarbonyl)pentyl)oxy]-2-(4-methoxy-phenyl)-1-[3-(N-methyl-N-(dimethylmethylcarbonyl)amino)propyl]-benzimidazole, 6-[(5-(Methoxycarbonyl)pentyl)oxy]-2-(4-methoxy-phenyl)-1-[3-(N-methyl-N-(methoxymethylcarbonyl)amino)propyl]-benzimidazole, and 6-[(5-(Methoxycarbonyl)pentyl)oxy]-2-(4-methoxy-phenyl)-1-[3-(N-methyl-N-(pyrid-3-yl-carbonyl)amino)propyl]-benzimidazole.

12. Pharmaceutical preparations that contain at least one benzimidazole derivative with general formula I according to claim 1 as well as at least one pharmaceutical vehicle.

13. A method of treating inflammatory or allergic diseases comprising administering an effective amount of a benzimidazole derivative with general formula I according to claim 1 to a patient in need thereof.

14. The method of claim 13 wherein the disease treated is stroke.

* * * * *